US010433725B2

(12) United States Patent
Byrns et al.

(10) Patent No.: US 10,433,725 B2
(45) Date of Patent: Oct. 8, 2019

(54) SYSTEM AND METHOD FOR CAPTURING SPATIALLY AND TEMPORALLY COHERENT EYE GAZE AND HAND DATA DURING PERFORMANCE OF A MANUAL TASK

(71) Applicant: THE GOVERNORS OF THE UNIVERSITY OF ALBERTA, Edmonton, Alberta (CA)

(72) Inventors: Simon Byrns, Edmonton (CA); Michael Feist, Edmonton (CA); Bin Zheng, Edmonton (CA); Pierre Boulanger, Edmonton (CA)

(73) Assignee: THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 227 days.

(21) Appl. No.: 15/702,522

(22) Filed: Sep. 12, 2017

(65) Prior Publication Data
US 2018/0070816 A1 Mar. 15, 2018

Related U.S. Application Data

(60) Provisional application No. 62/394,814, filed on Sep. 15, 2016.

(51) Int. Cl.
| G06K 9/00 | (2006.01) |
| H04N 7/14 | (2006.01) |
| A61B 3/113 | (2006.01) |
| G06K 9/62 | (2006.01) |
| A61B 5/11 | (2006.01) |

(52) U.S. Cl.
CPC ............... *A61B 3/113* (2013.01); *A61B 5/11* (2013.01); *G06K 9/00248* (2013.01); *G06K 9/00335* (2013.01); *G06K 9/00355* (2013.01); *G06K 9/00604* (2013.01); *G06K 9/00979* (2013.01); *G06K 9/6289* (2013.01); *A61B 5/1124* (2013.01); *A61B 5/1127* (2013.01); *G06K 2209/05* (2013.01)

(58) Field of Classification Search
USPC ........ 382/100, 103, 106–107, 117, 123, 128, 382/154, 155, 162, 168, 173, 181, 190, 382/199, 21, 6, 220, 232, 254, 274, 276, 382/285–294, 305, 312; 345/8
See application file for complete search history.

(56) References Cited

U.S. PATENT DOCUMENTS

2012/0235887 A1* 9/2012 Border ............... G02B 27/0093
345/8
2016/0342207 A1* 11/2016 Beran ..................... G06F 3/011
(Continued)

*Primary Examiner* — Seyed H Azarian
(74) *Attorney, Agent, or Firm* — Adler Pollock & Sheehan P.C.

(57) ABSTRACT

An eye gaze and hand data capturing system for use with a human performing a manual task (such as a surgical procedure) with a hand-held instrument (such as a surgical instrument), includes subsystems for tracking pupil position head position and orientation, hand position, and force applied by the hand to an instrument, all operatively connected to a computer that repeatedly determines an eye gaze vector, the hand position and orientation, and the force applied to the instrument and records such information as a record of spatially and temporally coherent data in a database.

14 Claims, 21 Drawing Sheets

(56) References Cited

U.S. PATENT DOCUMENTS

2017/0212988 A1\* 7/2017 Bertram ................. G16H 30/20
2017/0258526 A1\* 9/2017 Lang .................... H05K 999/99
2018/0260025 A1\* 9/2018 Messingher ............ G06F 3/012

\* cited by examiner

| Physical Array Marker | Mean Euclidian Distance (cm) | Gaze Angle Error (º) |
|---|---|---|
| 1 | 3.5 ± 2.0 | 3.0 ± 1.7 |
| 2 | 2.3 ± 1.0 | 2.1 ± 0.9 |
| 3 | 1.8 ± 1.0 | 1.5 ± 0.8 |
| 4 | 2.7 ± 1.5 | 2.4 ± 1.3 |
| 5 | 2.9 ± 1.5 | 2.4 ± 1.4 |
| 6 | 2.3 ± 1.4 | 2.0 ± 1.2 |
| 7 | 3.9 ± 2.4 | 3.6 ± 2.3 |
| 8 | 3.1 ± 1.3 | 2.4 ± 1.0 |
| 9 | 2.5 ± 1.6 | 2.1 ± 1.4 |

Fig. 26

| Virtual Array Marker | Mean Euclidian Distance (cm) | Gaze Angle Error (º) |
|---|---|---|
| 1 | 1.5 ± 0.2 | 1.3 ± 0.2 |
| 2 | 1.3 ± 0.4 | 1.0 ± 0.3 |
| 3 | 2.4 ± 0.7 | 1.9 ± 0.5 |
| 4 | 3.8 ± 1.8 | 3.1 ± 1.6 |
| 5 | 2.8 ± 0.2 | 2.2 ± 0.1 |
| 6 | 2.7 ± 0.7 | 2.2 ± 0.5 |
| 7 | 1.6 ± 0.5 | 1.4 ± 0.5 |
| 8 | 1.6 ± 0.3 | 1.3 ± 0.3 |
| 9 | 2.7 ± 1.3 | 2.1 ± 0.7 |
| 10 | 2.4 ± 0.1 | 1.9 ± 0.1 |
| 11 | 3.0 ± 0.5 | 2.4 ± 0.4 |
| 12 | 3.9 ± 1.4 | 3.0 ± 1.0 |
| 13 | 2.5 ± 0.8 | 2.0 ± 0.6 |
| 14 | 2.7 ± 0.7 | 2.2 ± 0.4 |
| 15 | 2.5 ± 1.9 | 1.9 ± 0.6 |

Fig. 27

| Target | Euclidean distance – gaze vector to target ± SD (cm) |
|---|---|
| 1 | 4.6 ± 1.3 |
| 2 | 2.5 ± 0.8 |
| 3 | 4.7 ± 0.9 |

| Target | Euclidean distance – Right D2 tip to target ± SD (cm) |
|---|---|
| 1 | 0.76 ± 0.06 |
| 2 | 0.86 ± 0.04 |
| 3 | 1.11 ± 0.13 |

SYSTEM AND METHOD FOR CAPTURING SPATIALLY AND TEMPORALLY COHERENT EYE GAZE AND HAND DATA DURING PERFORMANCE OF A MANUAL TASK

CROSS REFERENCE TO RELATED APPLICATION

This application claims the benefit of U.S. Provisional Patent Application Ser. No. 62/394,814, filed Sep. 15, 2016, the entirety of which is incorporated herein by reference (where permitted).

TECHNICAL FIELD

The present invention relates to capturing of eye gaze, hand motion, and hand force data during performance of a manual task, such as a surgical procedure.

BACKGROUND OF THE INVENTION

For certain tasks performed with hand-held instruments, such as surgical procedures, minute variations in hand-eye coordination and hand control may result in significant variations of skill and outcomes. Traditionally, a surgeon's skill is assessed by human observation of the surgeon performing a surgical procedure, whether live in person or in recorded video form. However, this method is subject to inherent limits of human observation, observer bias, and inter-observer variability. Thus, there remains a need for technological systems and methods for capturing eye gaze, hand motion and hand force data that can be used in objectively assessing the performance of a manual task.

SUMMARY OF THE INVENTION

An object of the present invention is capturing eye gaze data of a human. Another object of the present invention is capturing spatially and temporally coherent eye gaze and hand data (kinematic data and/or force data) for a human during performance of a manual task with a hand-held instrument.

Any term or expression not expressly defined herein shall have its commonly accepted definition understood by a person skilled in the art. As used herein, the term "instrument" refers to any hand-held tool including, without limitation, a hand-held surgical tool such as forceps, a clamp, a pair of scissors, or a needle driver. As used herein, the term "spatially and temporally coherent data" refers to two or more items of information that are or are capable of being correlated in space-time. For example, spatially coherent data includes data describing positional or orientation information that is or can be described in a common spatial coordinate system. For example, temporally coherent data includes information that is acquired in a synchronized manner at the same time, or that can be correlated in time such as by using a timestamp.

In one aspect, the present invention comprises an eye gaze data capturing system for use with a human comprising a pupil and a head, the system comprising:
(a) a pupil tracking subsystem for tracking a pupil position in two-dimensions;
(b) a head tracking subsystem for tracking a head position and orientation in three-dimensions; and
(c) a computer comprising a processor operatively connected to the pupil tracking subsystem, the head tracking subsystem and a memory comprising a non-transitory medium storing instructions readable by the processor to implement a method comprising the continuously performed steps of:
  (i) determining an eye gaze vector based on the pupil position, and the head position and orientation; and
  (ii) recording the eye gaze vector to a database.

In another aspect, the present invention comprises an eye gaze and hand data capturing system for use with a human comprising a pupil, a head, and a hand, the system comprising:
(a) a pupil tracking subsystem for tracking a pupil position in two-dimensions;
(b) a head tracking subsystem for tracking a head position and orientation in three-dimensions;
(c) a hand tracking subsystem for tracking a hand position and orientation in three-dimensions; and
(d) a computer comprising a processor operatively connected to the pupil tracking subsystem, the head tracking subsystem, the hand tracking subsystem, and a memory comprising a non-transitory medium storing instructions readable by the processor to implement a method comprising the repeatedly performed steps of:
  (i) determining an eye gaze vector based on the pupil position, and the head position and orientation; and
  (ii) recording to a database in the memory, a record of spatially and temporally coherent data comprising the eye gaze vector and the hand position.

In embodiments of the system, the pupil tracking subsystem comprises an eye camera for optically monitoring the pupil position.

In embodiments of the system, the head tracking subsystem comprises a plurality of markers attachable to the head, and at least one camera for optically capturing a position of the plurality of markers.

In embodiments of the system, the hand tracking subsystem comprises at least one electromagnetic sensor attachable to the hand, and at least one electromagnetic transmitter for generating an electromagnetic field detectable by the electromagnetic sensor. The at least one electromagnetic sensor may comprise a plurality of electromagnetic sensors, wherein each of the sensors is attached to different parts of the hand for sensing the position and orientation of different parts of the hand. The different parts of the hand may comprise one or a combination of different fingers of the hand and/or a hand dorsum.

In embodiments of the system, determining the eye gaze vector comprises:
(a) storing in the memory a plurality of known pairs of associated pupil positions and eye gaze vectors; and
(b) interpolating the eye gaze vector based on the stored plurality of known pairs of associated pupil positions and eye gaze vectors.

In embodiments of the system:
(a) the system further comprises an instrument force tracking subsystem for tracking a hand force applied to a hand-held instrument, wherein the processor is further operatively connected to the instrument force tracking subsystem; and
(b) recording to the database further comprises recording the hand force to the record as part of the temporally coherent data.

In embodiments of the system, the instrument force tracking subsystem comprises a piezoelectric sensor attachable to the hand-held instrument.

In embodiments of the system:
(a) the system further comprises a suture force tracking subsystem for tracking a tension force applied to a suture thread, wherein the processor is further operatively connected to the suture force tracking subsystem; and (b) recording to the database further comprises recording the tension force to the record as part of the temporally coherent data.

In embodiments of the system:
(a) the system further comprises at least one video recorder for generating a video signal encoding an image of the hand, wherein the processor is further operatively connected to the video recorder; and
(b) recording to the database further comprises recording the video signal to the record as part of the temporally coherent data.

In embodiments, the at least one camera comprises a first camera positioned to capture the image from a viewpoint approximating the point of view of the pupil, and a second camera positioned to capture the image from a viewpoint other than the viewpoint approximating the point of view of the pupil.

In embodiments of the system:
(a) the system further comprises at least one audio recorder for generating an audio signal encoding a sound of the human, wherein the processor is further operatively connected to the audio recorder; and
(b) recording to the database further comprises recording the audio signal to the record as part of the temporally coherent data of the record.

The systems and methods of the present method may be used to capture a rich and accurate dataset describing the human's eye gaze, hand movements and hand forces, during the performance of a manual task, such as surgery, without undue impairment of head and hand motions, or hand tactile sensations. The data recorded in the databases of the above systems can be analyzed to determine performance metrics using a variety of computation methods (e.g., Hidden Markov Models (HMM), Multivariate Autoregression (MAR), and Affine Velocity (AV) models) for segmenting movements into discrete head and hand gestures during performance of a manual task (or surgemes in the case of a surgical task), to assess the human's dexterity, and better understand iatrogenic (human caused) errors. The system may be incorporated into a manual task simulator that generates a performance score based on the data recorded in the databases, or that generates reference gaze, hand movement or hand force profiles for training purposes. Alternatively, the system may be used to capture data during performance of a manual task such as a surgical procedure, in a manner analogous to the use of a "black box" flight data recorder in avionics. Integration of this system into an operating room might allow for the detection of unsafe surgical maneuvers such as inappropriate force applied to tissue or eye and hand movement patterns that indicate surgeon fatigue. Thus this system has many potential applications in both training, quality improvement, and error analysis.

BRIEF DESCRIPTION OF THE DRAWINGS

Exemplary embodiments of the present invention are described with reference to the following drawings. In the drawings, like elements are assigned like reference numerals. The drawings are not necessarily to scale, with the emphasis instead placed upon the principles of the present invention. Additionally, each of the embodiments depicted is but one of a number of possible arrangements utilizing the fundamental concepts of the present invention. The drawings are briefly described as follows.

Figure 2:
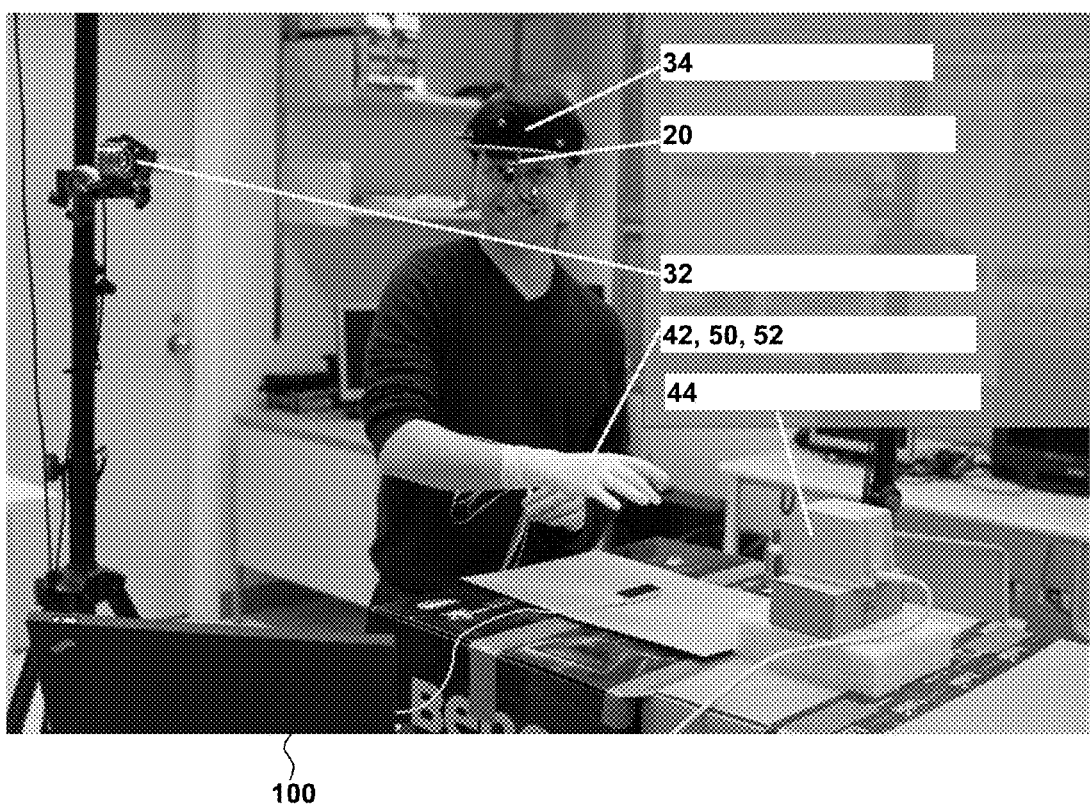
FIG. 2 shows an embodiment of the system of the present invention, when in use with a human.
Figure 21:
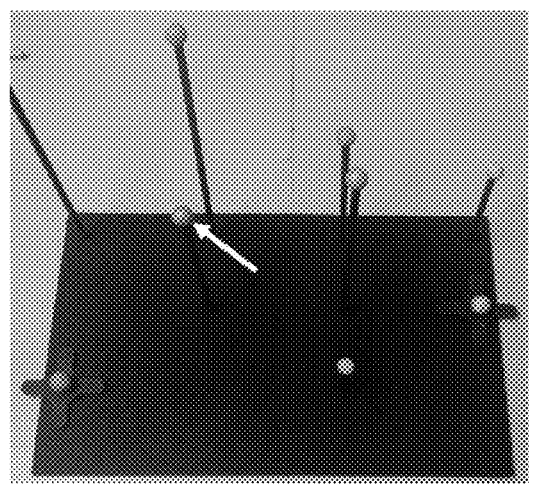
FIG. 21 shows an experimental set-up of a three-dimensional array of passive IR reflective markers used to verify the accuracy of 3D gaze vectors determined by the system of FIG. 2.
Figure 22:
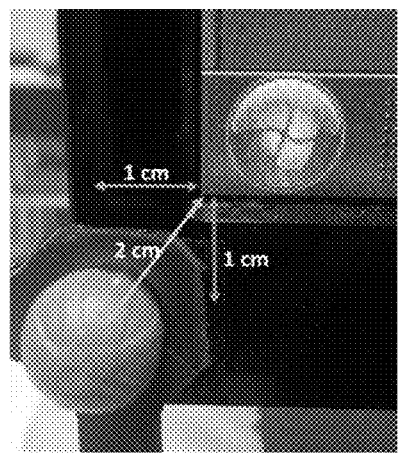
FIG. 22 shows an experimental set-up of a passive IR reflective marker on a computer monitor used to verify the accuracy of 3D gaze vectors determined by the system of FIG. 2.
Figure 25:
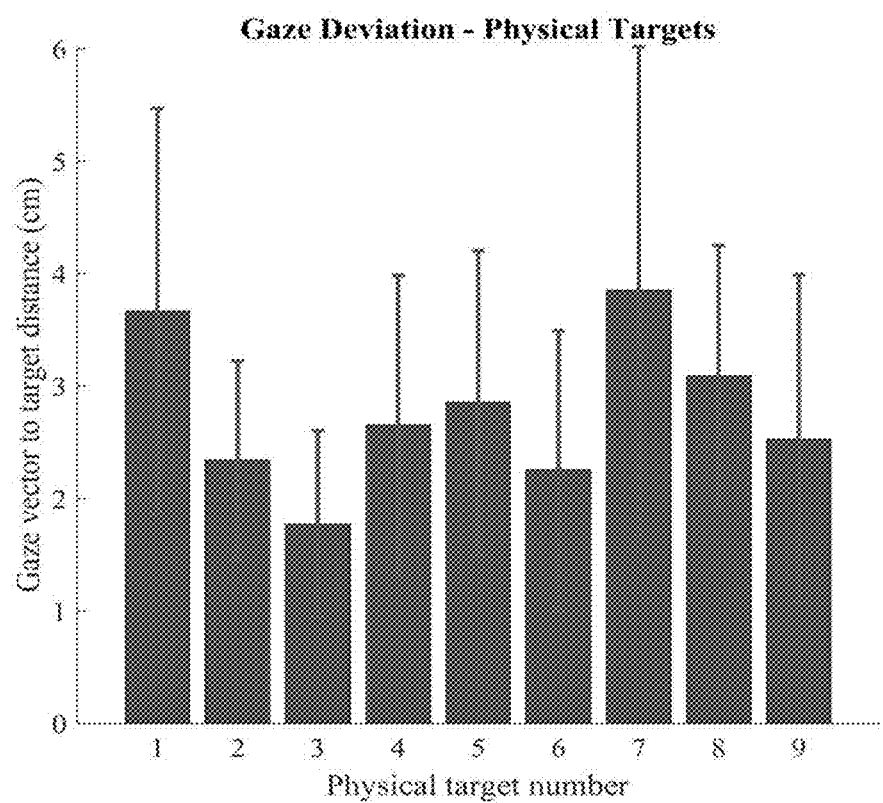
Figure 28:
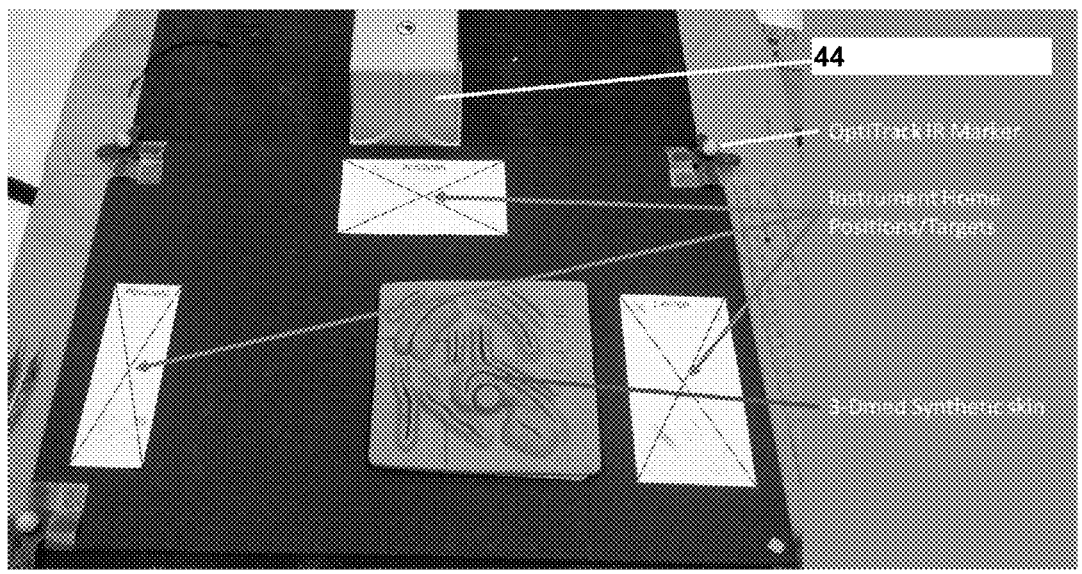
Figure 29:
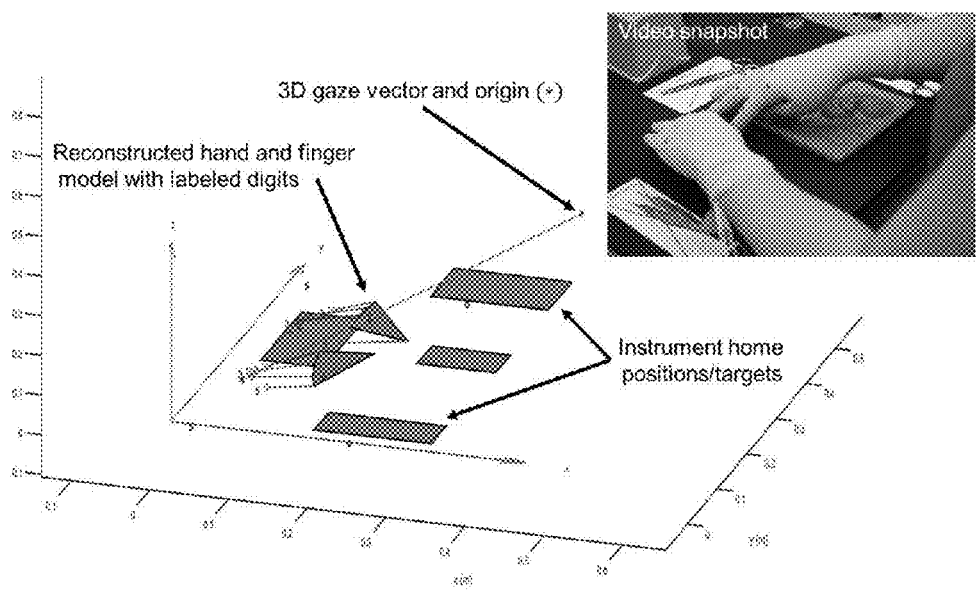
Figure 30:
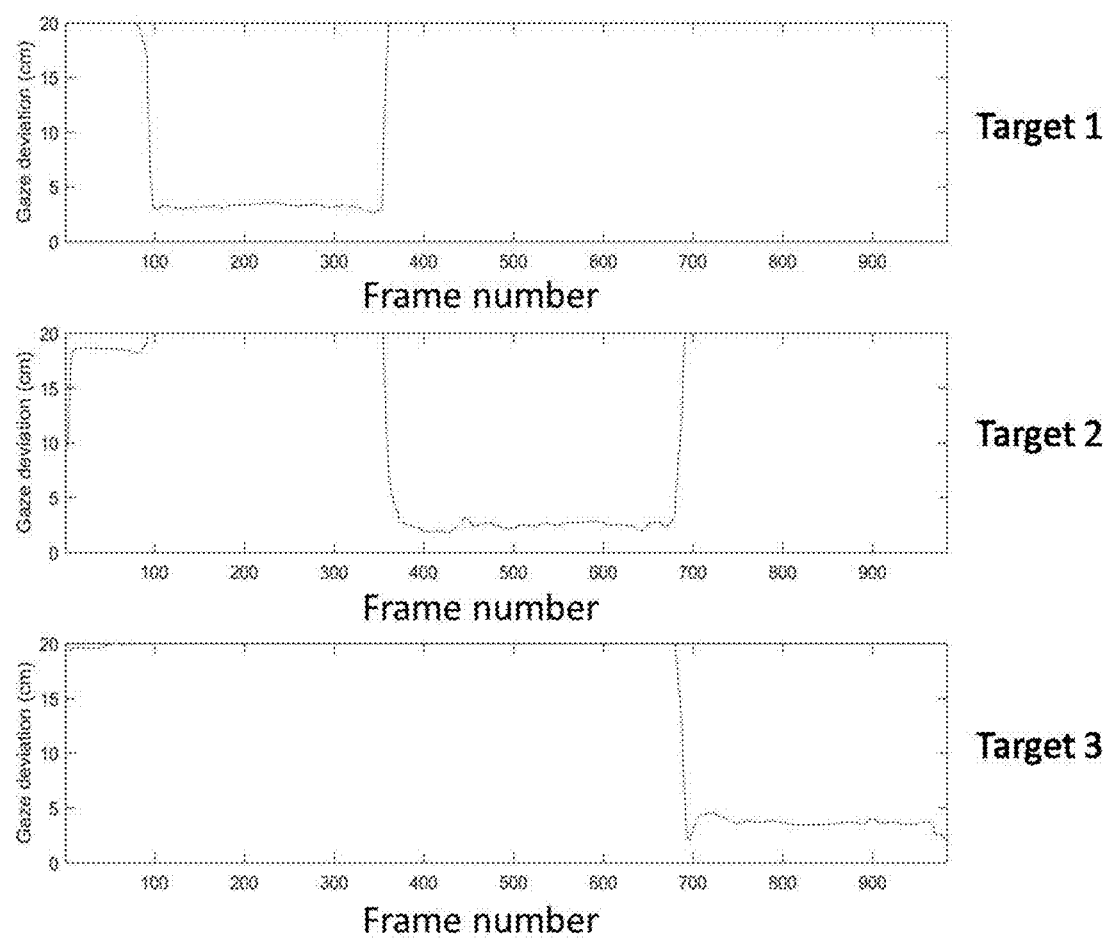
Figures 31, 32:
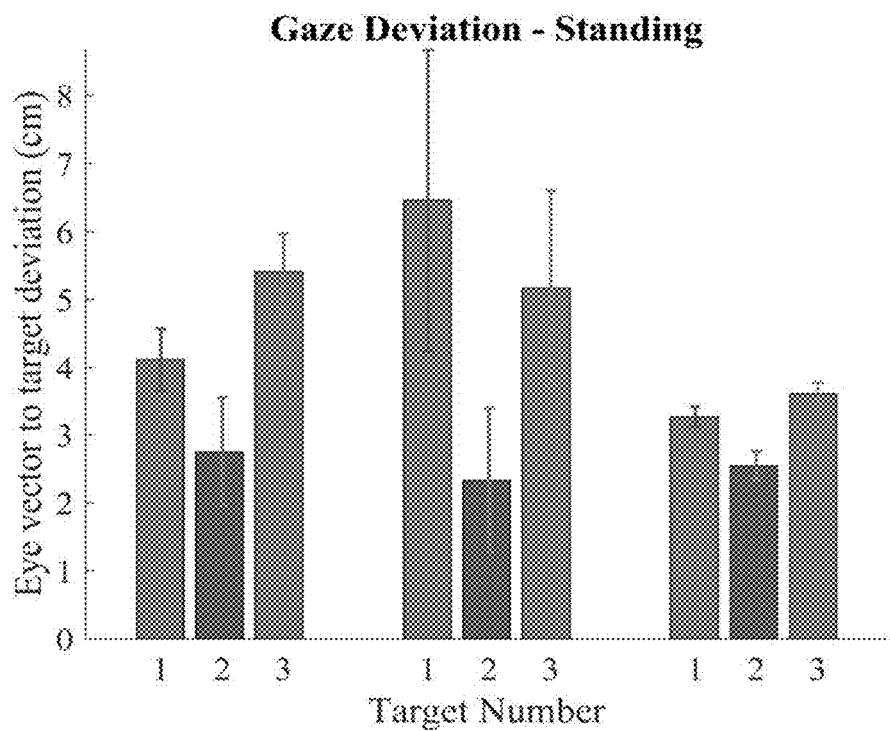
Figure 33:
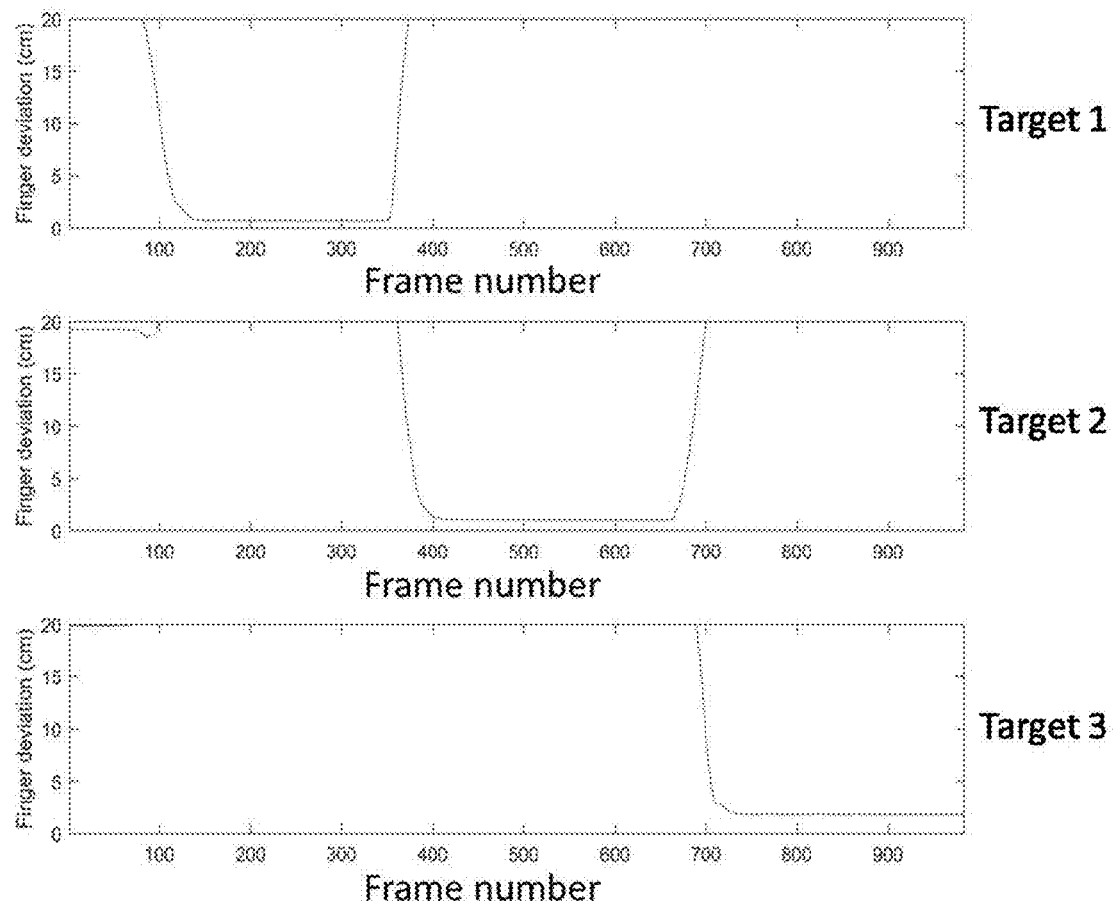
Figures 34, 35:
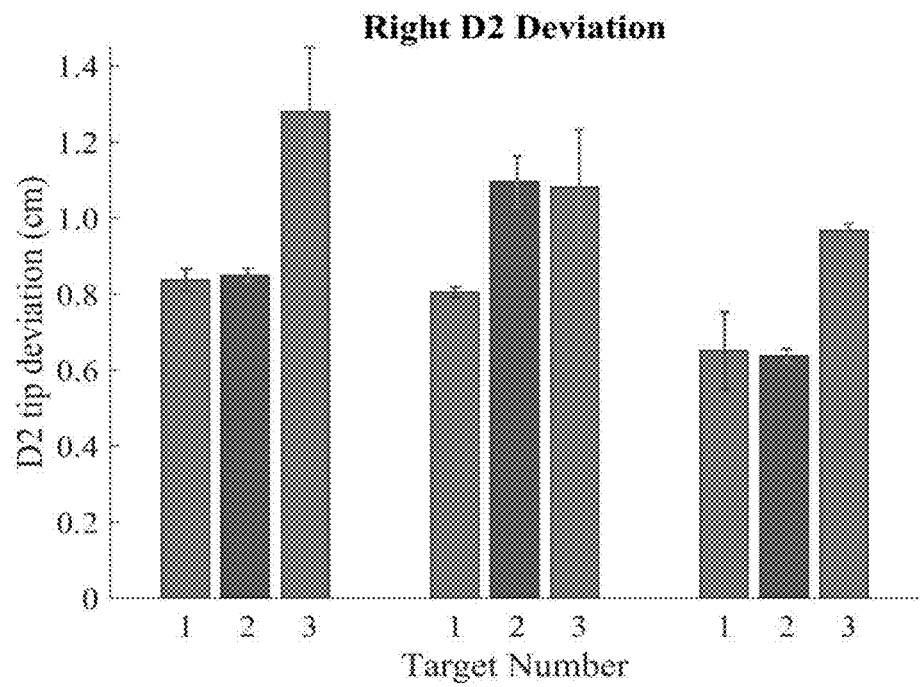

22, and a 3D gaze vector for virtual marker 2, as determined for a single participant in an experiment with the system of FIG. 2;

FIG. 25 is a graph showing the Euclidian distance and visual angle error for the physical IR marker array of FIG. 21, for a 3D gaze vector, as determined for a single participant in an experiment with the system of FIG. 2;

FIG. 26 is a table summarizing mean gaze distance and angle error for the physical IR marker array of FIG. 21, for 3D gaze vectors, as determined for multiple participants in an experiment with the system of FIG. 2;

FIG. 27 is a table summarizing mean gaze and angle error for a virtual marker array using the experimental set-up of FIG. 22, for 3D gaze vectors, as determined for multiple participants in an experiment with the system of FIG. 2;

FIG. 28 shows an experimental set-up for the system of FIG. 2, in relation to a simulated surgical work area and instrument home positions/targets;

FIG. 29 shows a MATLAB™ visualization of a surgeon's hands and eye gaze vector as determined by the system of FIG. 2, in the experimental set-up of FIG. 28, along with a video snap shot of same;

FIG. 30 shows a series of graphs comparing the distance between different targets and eye gaze vectors, as determined for a single participant in an experiment with the system of FIG. 2 in the experimental set-up of FIG. 28;

FIG. 31 shows a graph comparing the distance between the different targets and eye gaze vectors for three participants in an experiment with the system of FIG. 2 in the experimental set-up of FIG. 28;

FIG. 32 is a table summarizing the distance between the different targets and eye gaze vectors for three participants in an experiment with the system of FIG. 2 in the experimental set-up of FIG. 28;

FIG. 33 shows a series of graphs comparing the distance different targets and right index finger position, as determined for a single participant in an experiment with the system of FIG. 2 in the experimental set-up of FIG. 28;

FIG. 34 shows a graph comparing the distance between the different targets and right index finger position for three participants in an experiment with the system of FIG. 2 in the experimental set-up of FIG. 28; and FIG. 35 is a table summarizing the distance between the different targets and right index finger position for three participants in an experiment with the system of FIG. 2 in the experimental set-up of FIG. 28.

DETAILED DESCRIPTION OF THE INVENTION

Overview of the System (10)

Figure 1:
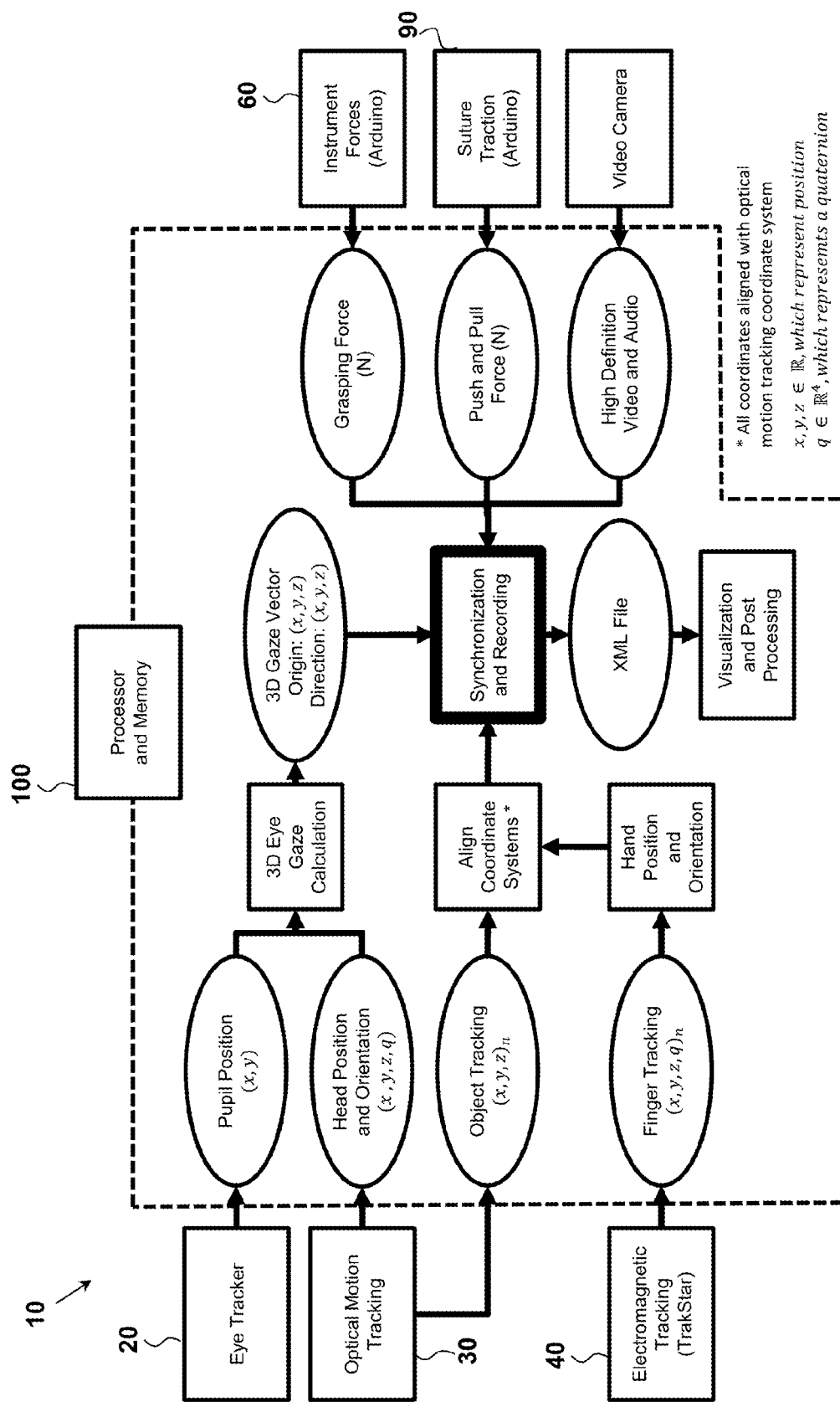
FIG. 1 is a schematic block-diagram of an embodiment of the system of the present invention.

FIGS. 1 and 2 show embodiments of a system (10) of the present invention for an exemplary use of capturing a data set describing a human surgeon's eye gaze, hand kinematic and hand force data during a surgical procedure. It will be understood that the system (10) may be used to capture data during a human's performance of other types of manual tasks, using other types of hand-held instruments, and that the present invention is not limited by any particular manual task or hand-held instrument.

In general, the exemplary embodiment of the system (10) comprises several tracking subsystems, audio-video recorders in the form of cameras, and an audio-visual display device operatively connected to a computer (100). The tracking subsystems comprise a pupil tracking subsystem (20), a head tracking subsystem (30), a hand tracking subsystem (40), an instrument force tracking subsystem (60), and a suture tension tracking subsystem (90). Exemplary embodiments of the system (10) components are now described in greater detail.

Pupil Tracking Subsystem (20)

A purpose of the pupil tracking subsystem (20) is to generate a signal indicative of a position of the surgeon's pupil in two dimensions. The pupil tracking subsystem (20) may comprise any suitable technology known in the art for pupil tracking. Pupil tracking technology is known in the art, and, in isolation, is not the present invention.

Figure 3:
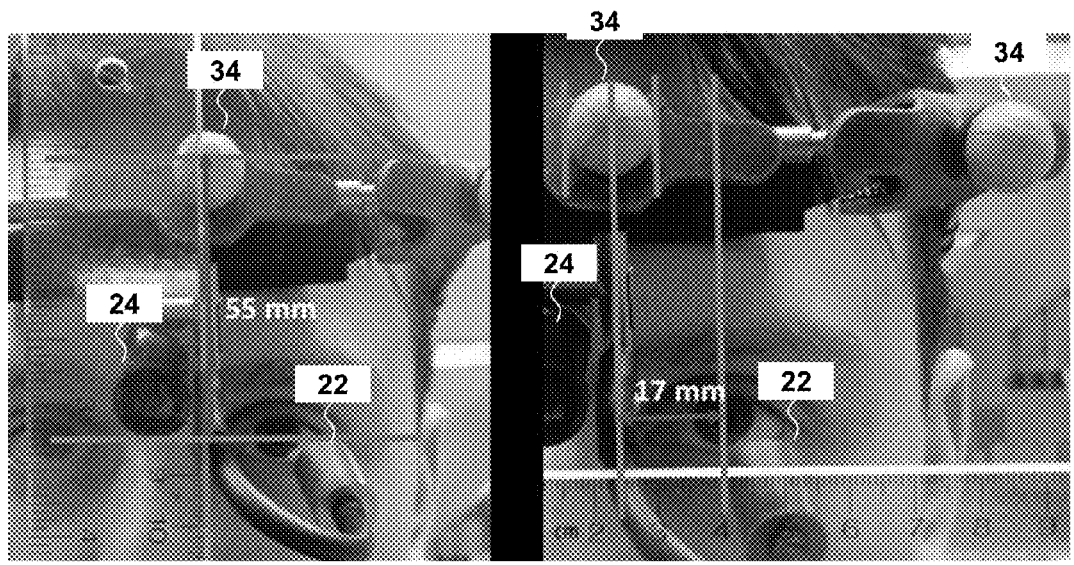
FIG. 3 shows the pupil tracking subsystem and the head tracking subsystem of the system of FIG. 2.
Figure 4:
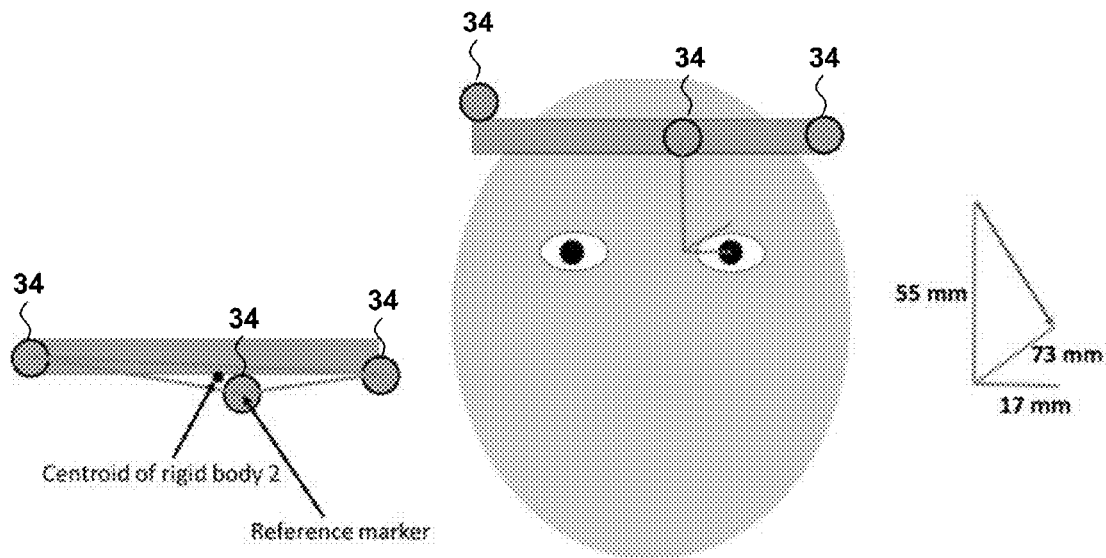
FIG. 4 shows the geometric offset of pupil position as determined by the pupil tracking subsystem and a passive IR marker of the head tracking subsystem of FIG. 3.

In the exemplary embodiment shown in FIGS. 2 and 3, the pupil tracking subsystem (20) comprises a Dikablis™ Monocular Eye Tracker system (10) (Ergoneers GmbH, Manching, Germany). The pupil tracking subsystem (20) comprises a frame worn on the surgeon's head with a first camera (an eye camera (22)) mounted below one the surgeon's eyes to capture pupil position, and a second camera (a field camera (24) that is a video recorder) mounted just above the surgeon's nose to capture an image of the environment approximating the point-of-view of the surgeon. The cameras are operatively connected to the computer (100) running Dikablis Recorder™ version 2.5 software. This software automatically provides functionality for streaming all pupil position data over a local area network using TCP/IP.

Head Tracking Subsystem (30)

A purpose of the head tracking subsystem (30) is to generate a signal indicative of the surgeon's head position and orientation in three-dimensions. The head tracking subsystem (30) may comprise any suitable means known in the art for 3-dimensional position tracking. Position tracking technology is known in the art, and in isolation, is not the present invention.

Figure 5:
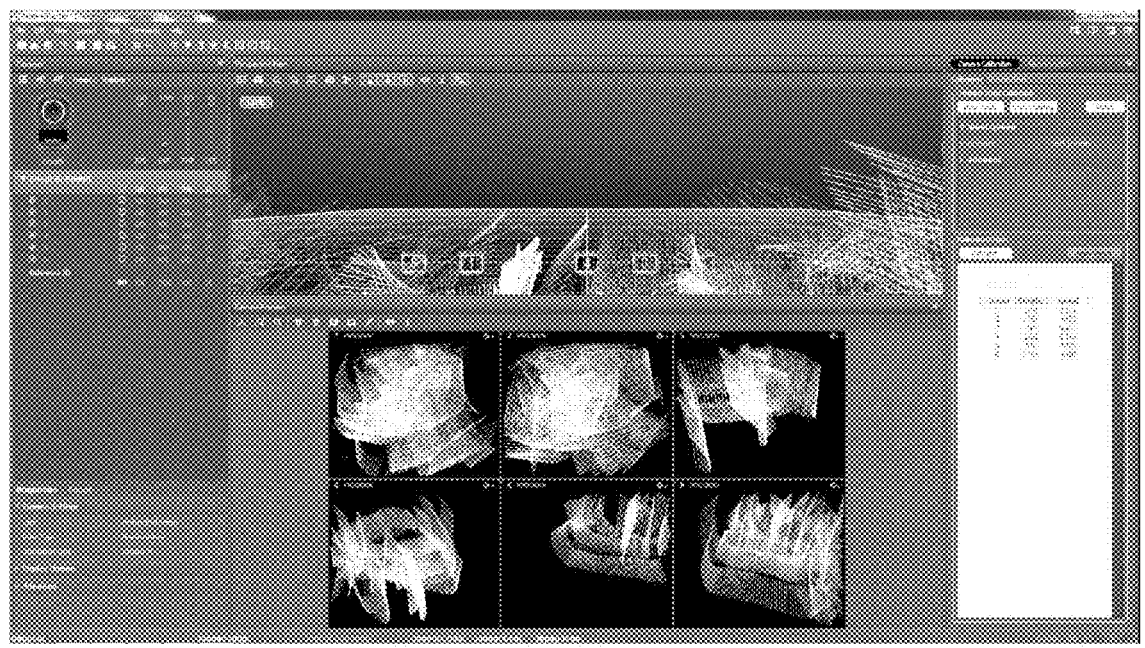
FIG. 5 shows a screenshot of a graphical user-interface generated by Motive™ software of the head tracking subsystem of FIG. 3.

In the exemplary embodiment shown in FIGS. 2 and 3, the head tracking subsystem (30) is an OptiTrack™ passive infrared (IR) motion capture system (NaturalPoint, Inc., Corvallis, Oreg.), which operates on optical motion tracking principles. The head tracking subsystem (30) comprises an array of six Flex-13 OptiTrack™ IR cameras (32), an LED IR source, and three passive IR markers (34) that are attached to the frame that also supports the eye-tracking camera of the pupil tracking subsystem (20) (as shown in FIG. 3) in an asymmetric triangular configuration. The IR cameras (32) are operatively connected to the computer (100) running Motive™ version 1.6 software (NaturalPoint, Inc., Corvallis, Oreg.). The IR markers were selected in the Motive™ software and labeled as rigid bodies in order to track their position in real-time. A screenshot of the graphical user interface of such software is shown in FIG. 5. Based on the software, the computer (100) receives electronic signals generated by the IR camera (32) to determine the three-dimensional position and orientation of the surgeon's head in an (x, y, z, q) coordinate system, with the variable "q" representing a quaternion.

Hand Tracking Subsystem (40)

A purpose of the hand tracking subsystem (40) is to generate a signal indicative of the position and orientation of the surgeon's hand or part thereof, in three-dimensions. The hand tracking subsystem (40) may comprise any suitable means known in the art for 3-dimensional position tracking. Position tracking technology is known in the art, and in isolation, is not the present invention.

Figure 6:
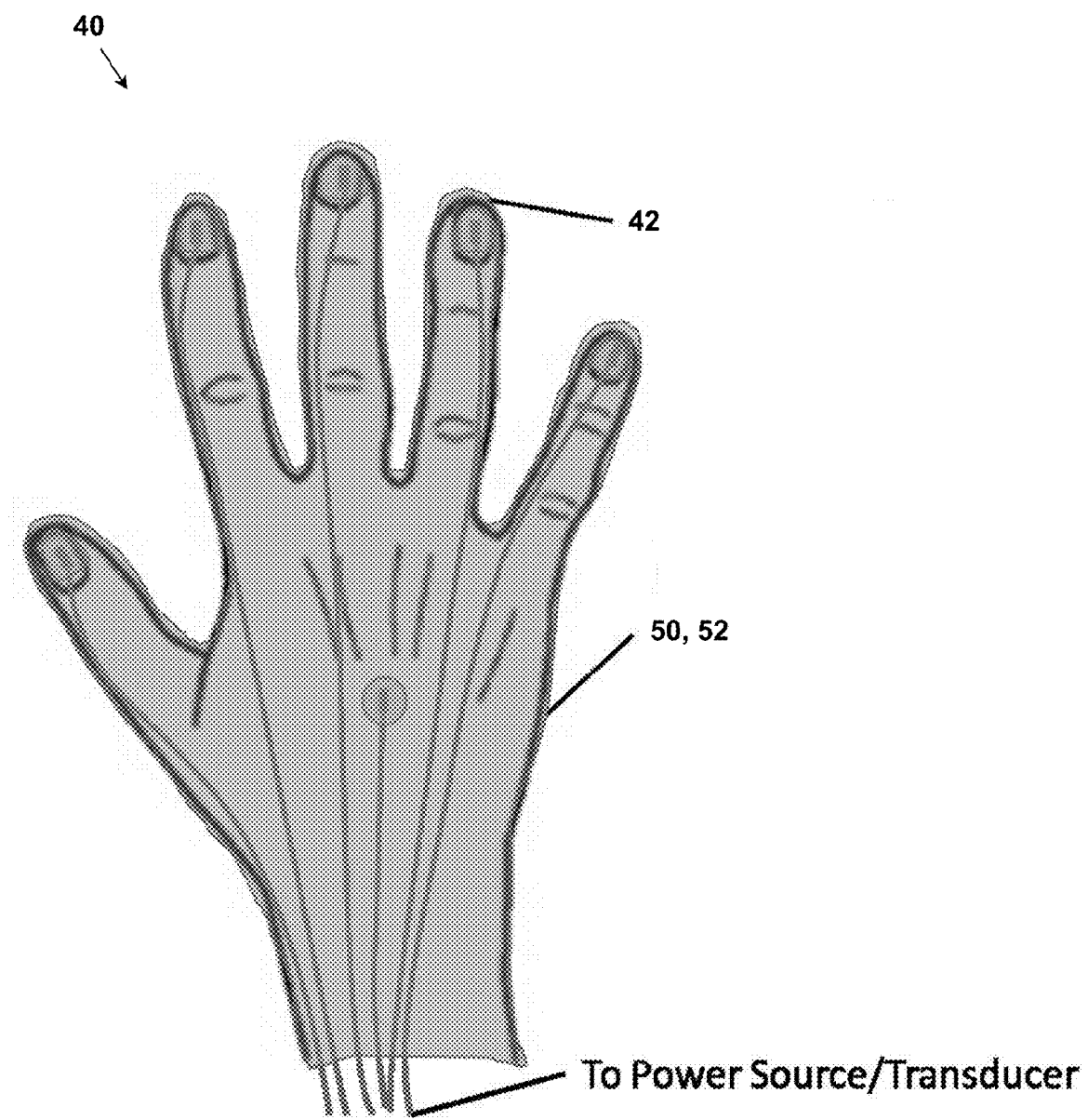
FIG. 6 shows a dorsal view of a hand wearing the hand tracking subsystem of the system of FIG. 2.
Figure 7:
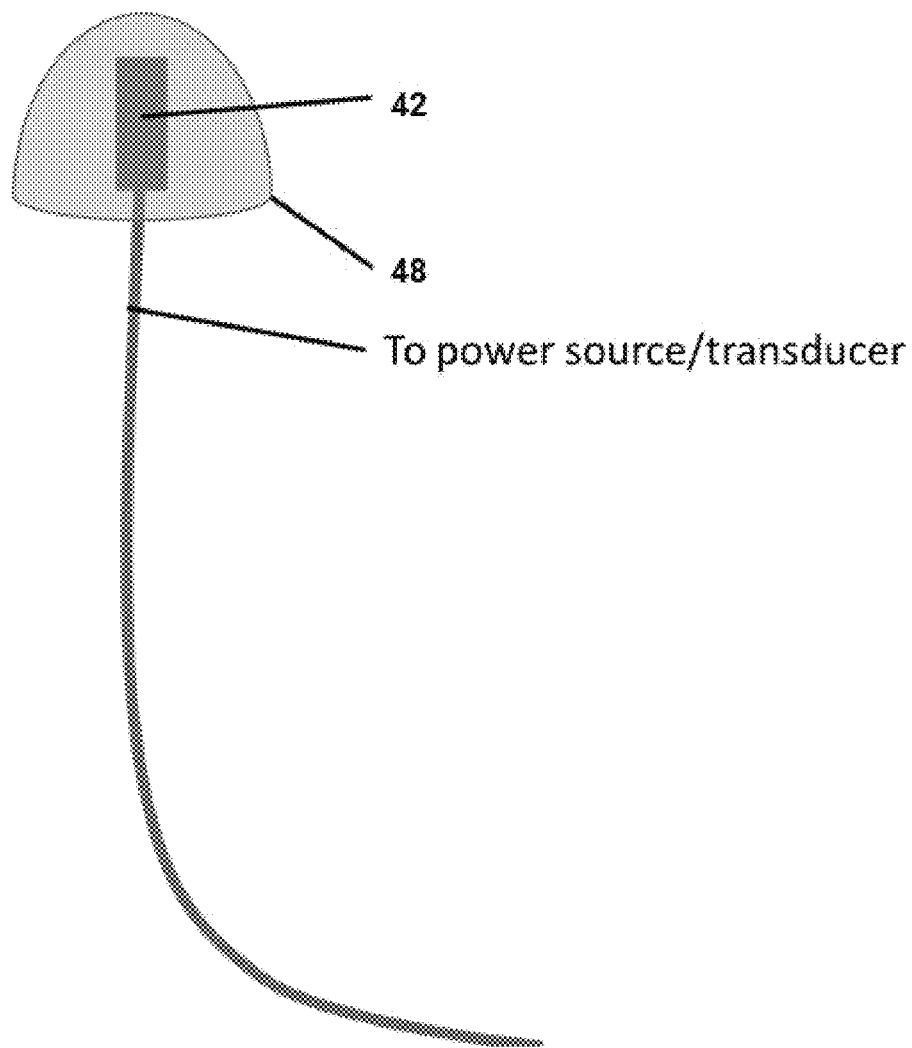
FIG. 7 shows a dorsal view of part of the hand tracking subsystem of FIG. 6.
Figure 8:
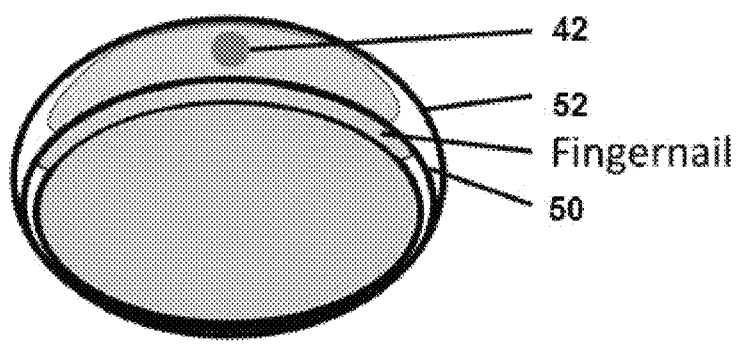
FIG. 8 shows a transverse cross-sectional view of a finger wearing the hand tracking subsystem of FIG. 6.

In the exemplary embodiment shown in FIGS. 6 to 8, the hand tracking subsystem (40) is designed to provide an accurate and detailed determination of the position and orientation of each of the surgeon's finger tips and the hand dorsum, with minimal impediment to the surgeon's hand and finger movement, and tactile feedback.

In the exemplary embodiment shown in FIG. 6, the hand tracking subsystem (40) operates on electromagnetic (EM) sensing principles. The hand tracking subsystem (40) comprises a plurality of EM sensors (42) integrated on a glove worn by the surgeon, which are multiplexed with a Track-STAR™ EM transmitter/transducer (44) (Acension Technology Corp., Shelburne, Vt.), which is turn operatively connected to the computer (100). In the exemplary embodiment shown in FIGS. 7 and 8, each EM sensor (42) is a small 1.5 mm outer diameter EM sensor (42) to minimize the bulkiness of the hand tracking system (40).

Figure 9:
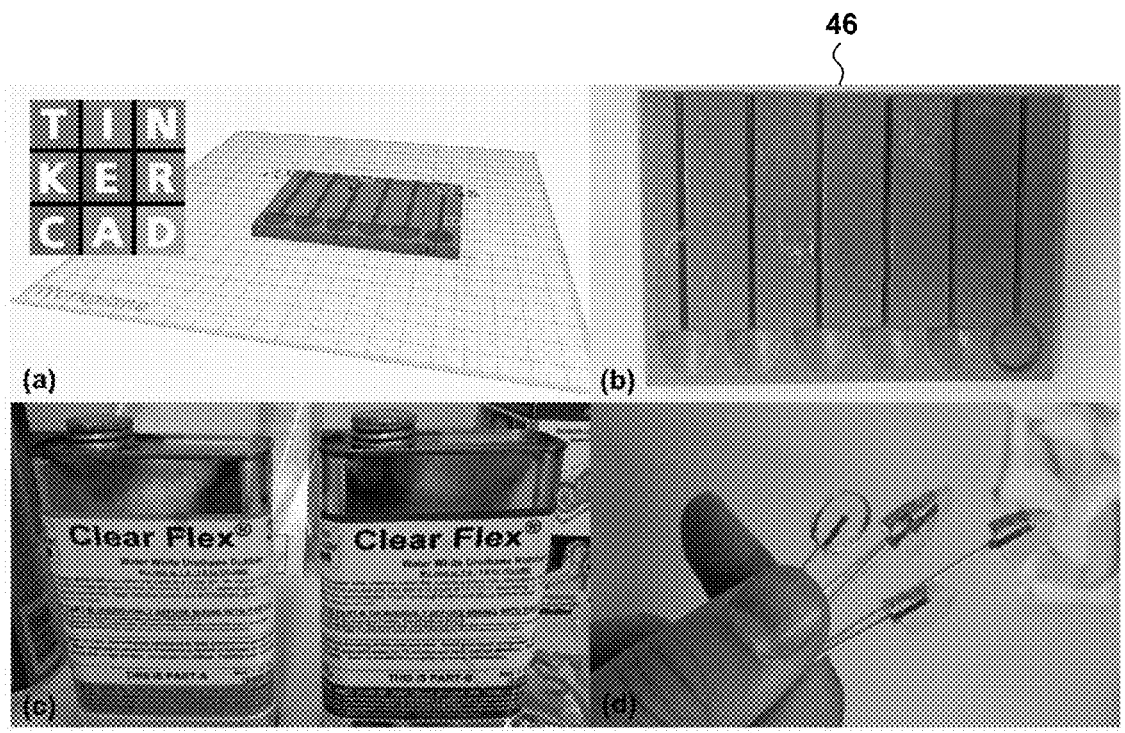
FIG. 9 shows different stages in the fabrication of encapsulated EM sensors in the hand tracking subsystem of FIG. 6.

In order to protect and maintain the orientation of each EM sensor (42), each EM sensor (42) is encapsulated in an encapsulation material (48), which in exemplary embodiments is a transparent urethane plastic material, or rubber or silicone material. FIG. 9 shows different stages in fabrication of encapsulated EM sensors (42). In FIG. 9, step (a), TinkerCAD™ (Autodesk, San Rafael, Calif.), a web-based HTML5/WebGL computer aided design tool, was used to design the encapsulation mold (46) for the EM sensors (42). Each mold (46) defines a well that is 2.8 mm deep and 12 mm wide to minimize the amount of material necessary for encapsulation of the EM sensor (42) and allows fixation on small and large fingernails. In FIG. 9, step (b), the mold (46) was 3D printed on a 3D printer at high resolution (0.02 mm) and sealed with XTC-3D™ protective coating (Smooth-On Inc., Macungie, Pa.). In FIG. 9, step (c), two encapsulation materials (48) were tested including Encapso-K™ rubber and Clearflex-30™ urethane rubber (Smooth-On Inc., Macungie, Pa.). Both are pliable with a Shore A hardness of 30. Encapsulation with Encapso-K™ was successful but the material was too friable in repeated testing. Clearflex 30™ was subsequently used, but required additional preparation including vacuum degassing which was accomplished with a commercially available Foodsaver V2040™ vacuum sealer and canister (Sunbeam, Boca Raton, Fla.). In FIG. 9, step (d), following encapsulation and approximately 72 to 96 hours of hardening time, the encapsulated sensors were removed from the 3D mold (46) and excess material was trimmed from the edges. A total of twelve Model 130™ EM sensors (42) (NDI, Waterloo, Ontario) were encapsulated in order to instrument each finger and the dorsum of each hand.

Referring again to the exemplary embodiment of FIGS. 7 and 8, after donning a first inner pair of Encore™ surgical gloves (50) (Ansell, Iselin, N.J.), five encapsulated EM sensors (42) were fixed to dorsal aspect of each finger over the nailbed using a small amount of cyanoacrylate. A second pair of Encore™ gloves (52) were then placed over the first pair of gloves and the encapsulated EM sensors (42, 48). The cables for each encapsulated EM sensor (42, 48) were positioned to run along the medial or lateral aspect of each finger in order to facilitate normal finger flexion. The sixth encapsulated EM sensor (42, 48) on each hand was placed over the dorsal aspect of the midpoint of the third metacarpal.

In the exemplary embodiment shown in FIG. 2, all twelve encapsulated EM sensors (42) were connected to an NDI 3D Guidance TrakSTAR™ system consisting of 3 units operating in multi-unit sync (MUS) mode with a single transmitter magnet. This system was connected to the main computer (100) via a USB interface. The synchronization and recording software utilized the application program interface (API) to initialize and capture each EM sensor's (42) position and orientation at a frequency of 60 Hz. While the TrakSTAR™ system permits the polling of sensor position at much higher frequencies (>100 Hz), testing showed that reducing the frequency resulted in less noise and interference.

Instrument Force Tracking Subsystem (60)

Figure 10:
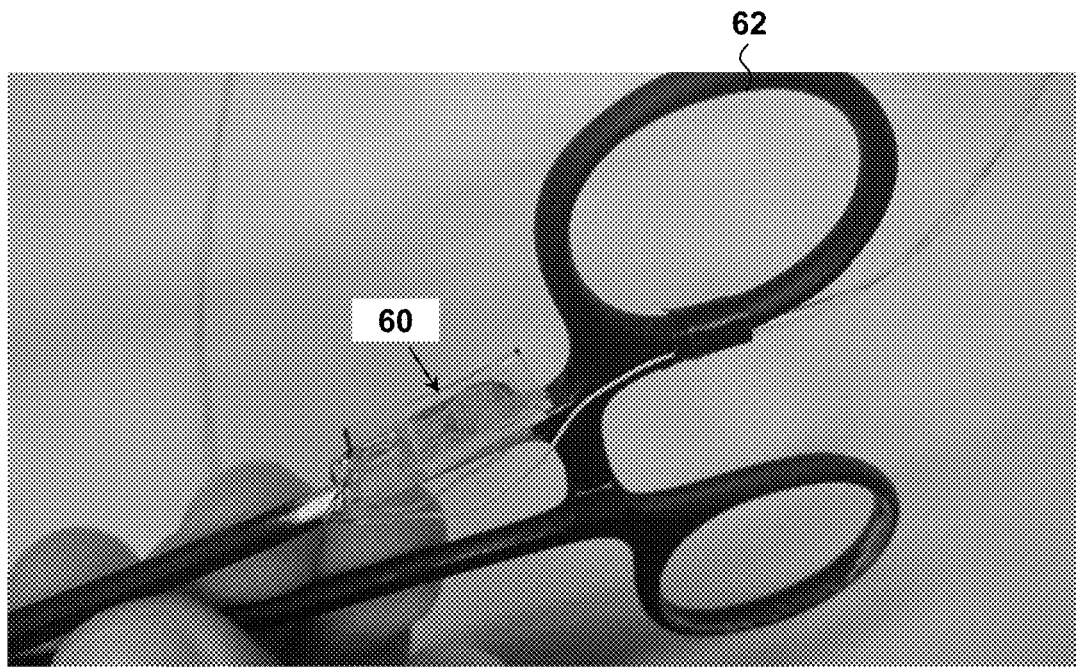
FIG. 10 shows surgical needle driver with an attached instrument force tracking subsystem of the system of FIG. 2.
Figure 11:
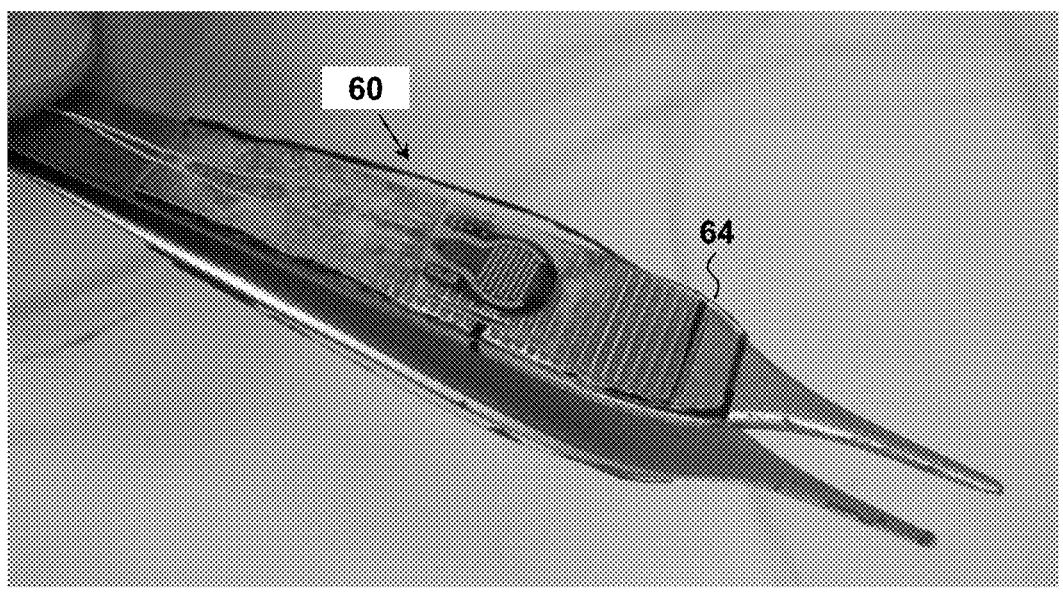
FIG. 11 shows surgical forceps with an attached instrument force tracking subsystem of the system of FIG. 2.
Figure 12:
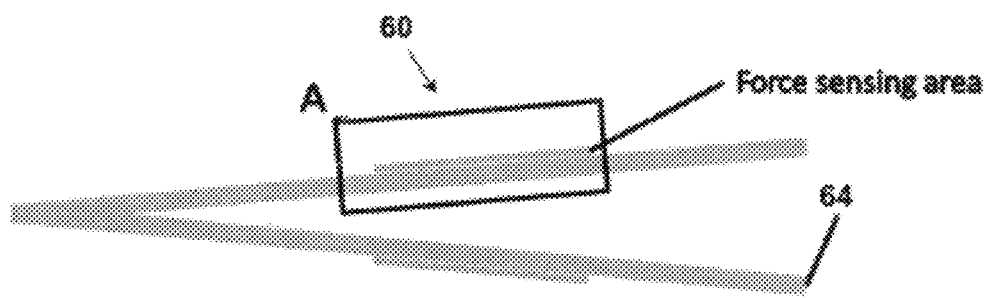
FIG. 12 shows a side view of surgical forceps with an attached instrument force tracking subsystem of FIG. 11.

A purpose of the instrument force tracking subsystem (60) is to measure the amount of force applied by the surgeon's hand to one or more surgical instruments. The surgical instrument can be any hand-held surgical instrument, including without limitation, one or a combination of a surgical clamps, scissors or a needle driver (62) (as shown in FIG. 10) or surgical forceps (64) (e.g., Debakey or Adson style forceps (64)) (as shown in FIGS. 11 and 12). The instrument force tracking subsystem (60) comprises any suitable force sensor known in the art for measuring applied force. Force sensors are known in the art, and in isolation, are not the present invention.

Figure 13:
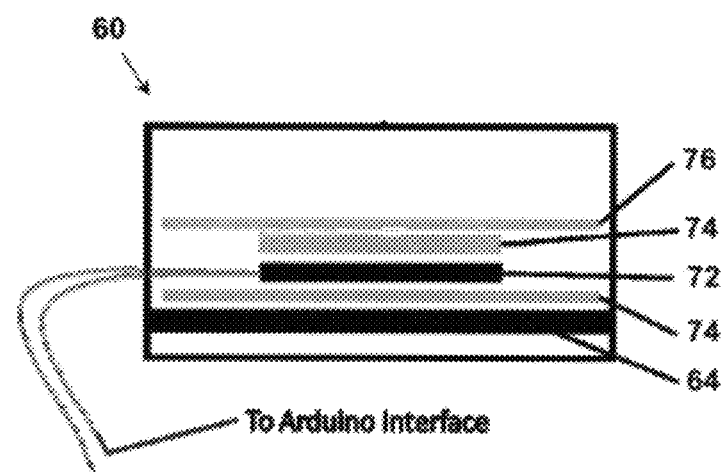
FIG. 13 shows a detailed view of the instrument force tracking subsystem in region "A" of FIG. 12.
Figure 14:
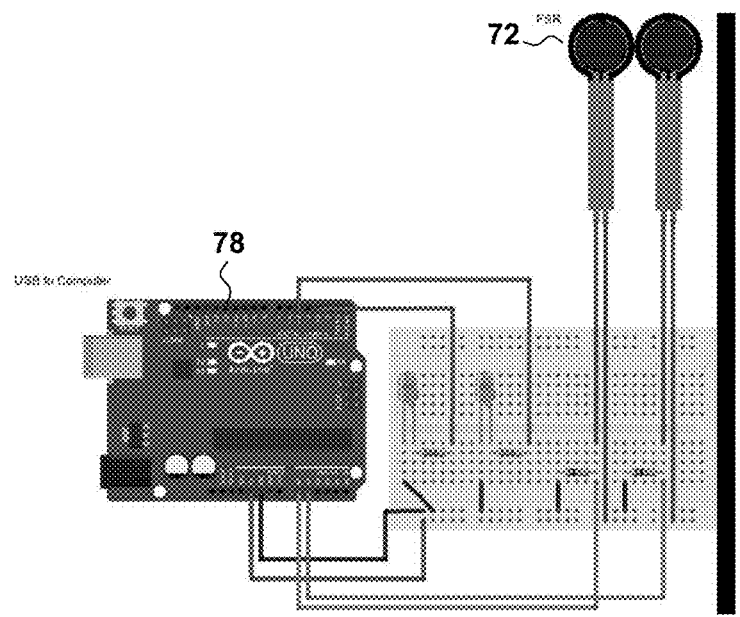
FIG. 14 shows a schematic of an Arduino™ microcontroller circuit board interfaced with force sensors of the instrument force tracking subsystem of FIG. 11.
Figure 15:
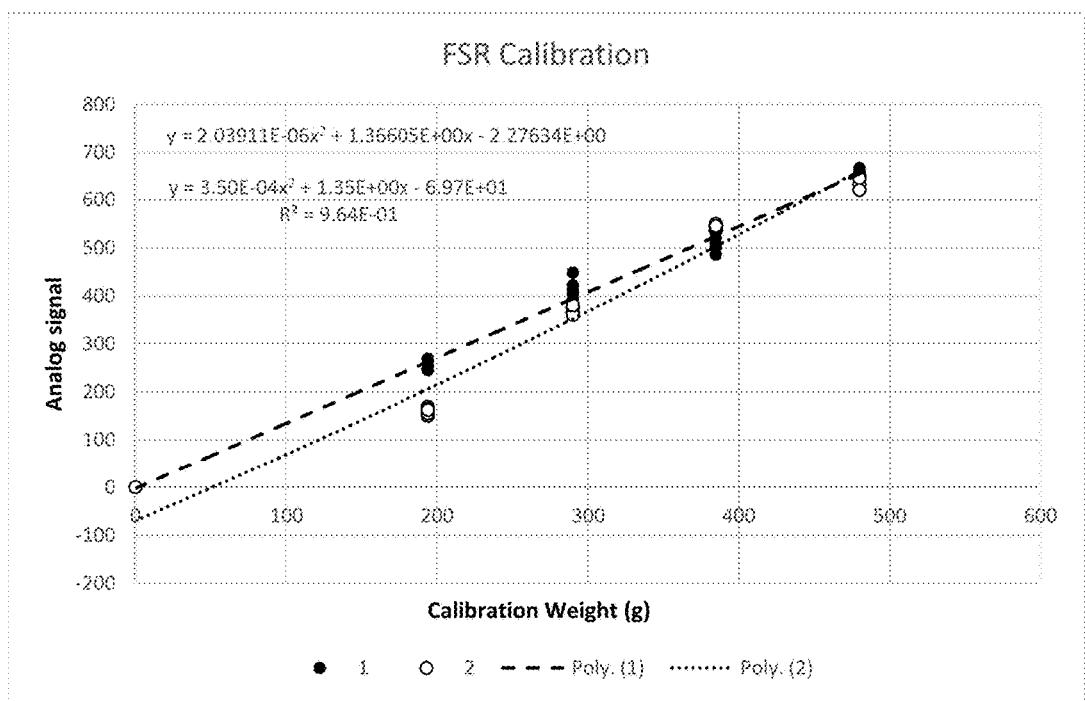
FIG. 15 shows second degree polynomial calibration curves for two force sensors of the instrument force tracking subsystem of FIG. 11.

In the exemplary embodiment, the force sensors are selected to minimize the bulkiness of the sensors used in the instrument force tracking subsystem (60), with minimal reduction in the normal tactile feedback to the surgeon's hands when using the forceps (64). The force sensors are in the form of piezoelectric force sensitive resistors (FSRs) (72) (Interlink Electronics, Westlake Village, Calif.) that can be used to determine forces applied to the active area of the FSR (72) sensor by measuring resistance across the FSR (72) (i.e., resistance increases as the applied force increases). As shown in an exemplary embodiment in FIGS. 12 and 13, two FSRs (72) were fixed to a pair of Adson forceps (64) at the typical position for the thumb and forefinger. As shown in FIG. 13, a 1.5 mm thick dielectric/interface silicon elastomer layer (74) was positioned over the active area of the FSR (72) and a thin, transparent 0.5 mm PVC plastic layer (76) was placed over this to create the final sensor sandwich. An Arduino™ microcontroller circuit board (78) was used to interface with the FSRs (72) and provide a means for recording the resistance measurements and translate these into force in Newton units following a polynomial calibration procedure. FIG. 14 shows a schematic of the Arduino™ microcontroller circuit board (78) interfaced with the FSRs (72). A set of standard weights were used to calibrate the sensor over a range of 150 g to 500 g, with 6 replicate recordings for each weight. FIG. 15 shows the second degree polynomial calibration curve for two of the FSRs (72).

Suture Tension Tracking Subsystem (90)

Figure 16:
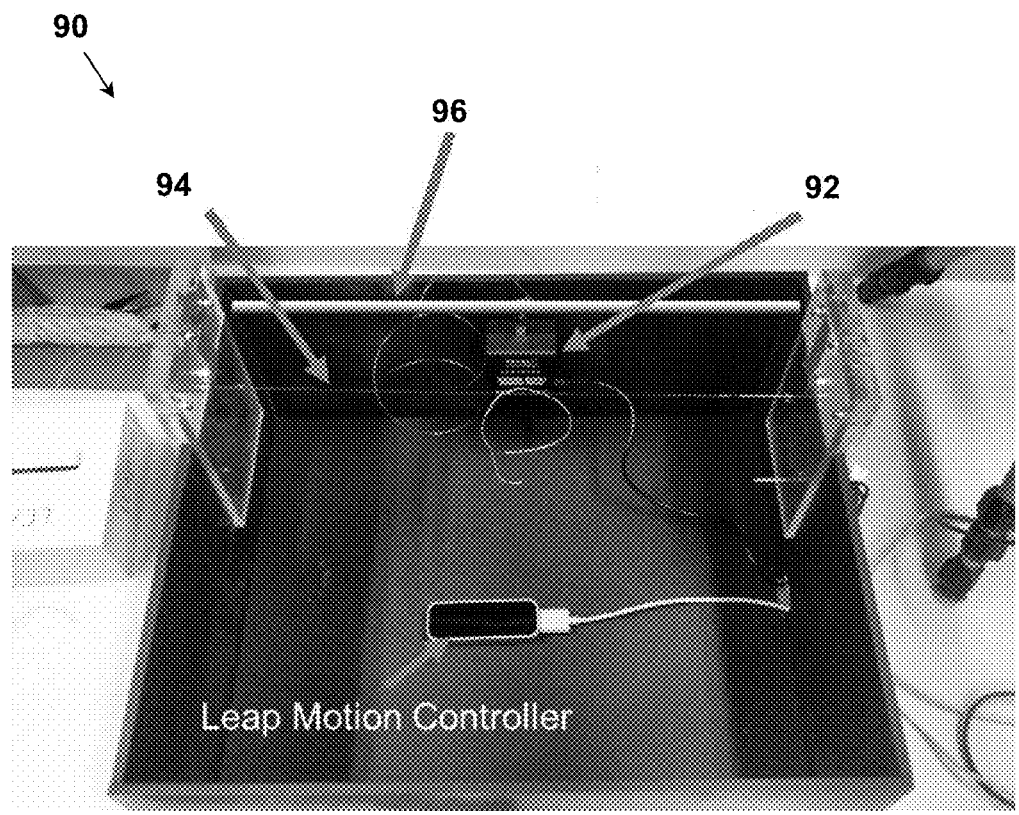
FIG. 16 shows a surgical knot tying simulator with integrated dual range force sensor.

Many surgical procedures require the delicate application of tension to a suture while performing hand ties, e.g., ligation of small vessels. FIG. 16 shows a surgical knot tying simulator with integrated dual range force sensor (92) for measuring the tension force applied to the suture thread (94). In a similar fashion as demonstrated by Hsu et al. (Hsu J L, Korndorffer J R, Brown K M. Design of vessel ligation simulator for deliberate practice. J Surg Res 2015; 197(2): 231-235), a dual range force sensor (92) (Vernier Software and Technologies, Beaverton, Oreg.) was attached to a suture thread (94) (e.g., nylon monofilament) under tension. However, an additional 'pulley' in the form of a non-ferromagnetic aluminum rod (96) was introduced to translate any forces applied to the suture thread (94) into the vertical axis, ensuring alignment with the axis of the force sensor. This approach is likely more robust than that presented by Hsu et al., as forces applied orthogonally to the force sensor without this pulley would not be detected.

Computer (100)

The computer (100) comprises a processor, and an operatively connected memory comprising a non-transitory computer readable medium storing instructions executable the processor to implement steps of a method of the present invention as described below.

In exemplary embodiments, the processor may comprise one or a combination of a microprocessor (i.e., a computer (100) processor on an integrated circuit device), a field-programmable gate array (FPGA), which may be part of a general purpose computer (100) or a special purpose computer (100), a central processing unit (CPU), a computing devices, microcontrollers, signal processors, or like devices.

In exemplary embodiments, the memory may comprise a volatile memory (i.e., memory that requires power to maintain the stored data) as well as a non-volatile memory (i.e., memory that can be retrieved after power to the memory has been cycled on and off). In exemplary embodiments, the memory may comprise solid-state flash memory, other types of non-transitory computer readable media (e.g., magnetic media, and optical media), as known to persons skilled in the art.

Although reference may be made to a computer (100), processor and memory as singular components, it will be understood that the foregoing terms may refer to a plurality of components operatively connected to each other, irrespective of whether such components are physically integrated with each other or physically distributed, and irrespective of whether such component or components are considered to be functionally part of the aforementioned subsystems (20, 30, 40, 60, 90). Operative connections between the computer components may include one or a combination of wired connections (e.g., metallic connections, fiber optics, and the like) or wireless connections (e.g., via radio frequency (RF) and infrared (IR) signals, and other electromagnetic signal transmissions).

It will be appreciated that use and operation of the system (10) may be preceded by calibration steps within the skill of the person of ordinary skill in the art to verify the accuracy of the data generated by the system (10) within certain operating parameters (e.g., a viewing distance between the surgeon's head and the surgeon's hands of about 55-85 cm).

Methods of the Present Invention

Exemplary embodiments of methods of the present invention, as implemented by the system (10) of the present invention, are now described.

Step 1: Reception and Recording of Raw Data from Subsystems

During use and operation of the system (10), data is continuously received simultaneously in real time from the aforementioned subsystems and stored in a database of the memory of the computer memory. It will be understood that a database may comprise a data structure for representation of information in a particular format such as a relational databases, object-based models and/or distributed databases. In addition, the databases may, in a known manner, be stored locally or remotely from a device which accesses data in such a database.

In an exemplary embodiment, raw data is streamed from the subsystems to custom developed recording software using NAT-Net and TCP/IP network protocols. The raw subsystem data is saved in a database using a system-generated timestamp to ensure temporal coherence for subsequent analysis.

Step 2: Alignment of Coordinate Systems of Head Tracking Subsystem (30) and Hand Tracking Subsystem (40)

If the raw data generated by the head tracking subsystem (30) and hand tracking subsystem (40) are not in a common coordinate system (10), then it is necessary to align their coordinate systems (10) to preserve spatial coherence between them.

In an exemplary embodiment, this is achieved by calibrating the EM sensors (42) of the hand tracking subsystem (40) using an L-Frame of optical IR markers registered to the OptiTrack MoCap™ platform of the head tracking subsystem (30). In order to both visualize and analyse the recorded head tracking data and hand tracking data, a parsing script is implemented in MATLAB™ to reorient all of the data into a shared coordinate system (10). For example, the position of a tracked object or surface in OptiTrack™ was rotated 90 degrees clockwise about the X axis according to equation (1):

$$P = (x_{MatLab}, y_{MatLab}, z_{MatLab}) = (x_{OptiTrack}, z_{OptiTrack}, y_{OptiTrack}) \quad (1)$$

Figure 17:
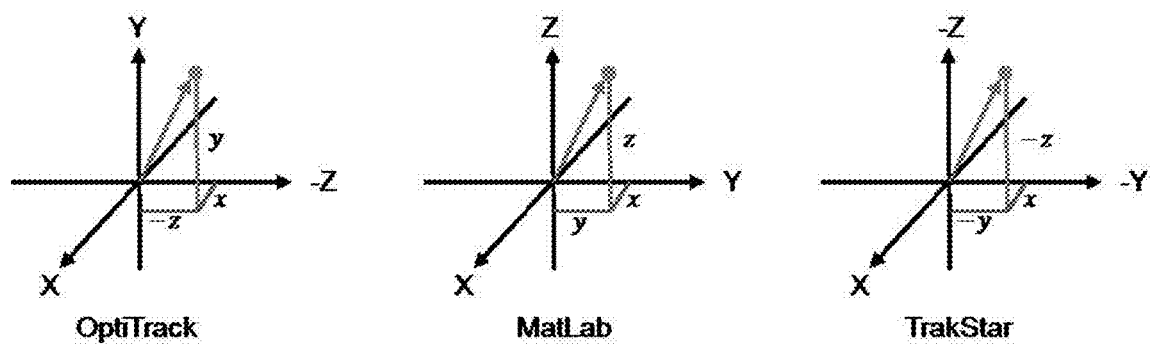
FIG. 17 shows orientations of the coordinate systems for the head tracking subsystem, and the hand tracking subsystem, and the computer in the system of FIG. 1.

FIG. 17 shows a diagram of the different orientations of the coordinate systems for the head tracking subsystem (30) (labelled OptiTrack), the hand tracking subsystem (40) (labelled TrakStar) and the software of the computer (100) (labelled MatLab). All the coordinate systems were right handed, necessitating rotational transformations to achieve spatial coherence.

Step 3: Generation of 3D Gaze Vector

A purpose of this step is to determine a 3D gaze vector describing an origin location and direction of the surgeon's eye gaze, by combining the pupil position data generated by the pupil tracking subsystem (20) and the head position and direction data generated by the head tracking subsystem (30).

In an exemplary embodiment, once the 3D gaze vector is determined, it is recorded in the database, along with the timestamped positional data generated by the head tracking subsystem (30), and hand tracking subsystem (40), into a compressed XML file for offline analysis. Each 3D gaze vector is saved as a pair of two coordinates representing the origin and a second point on the gaze vector.

Figure 18:
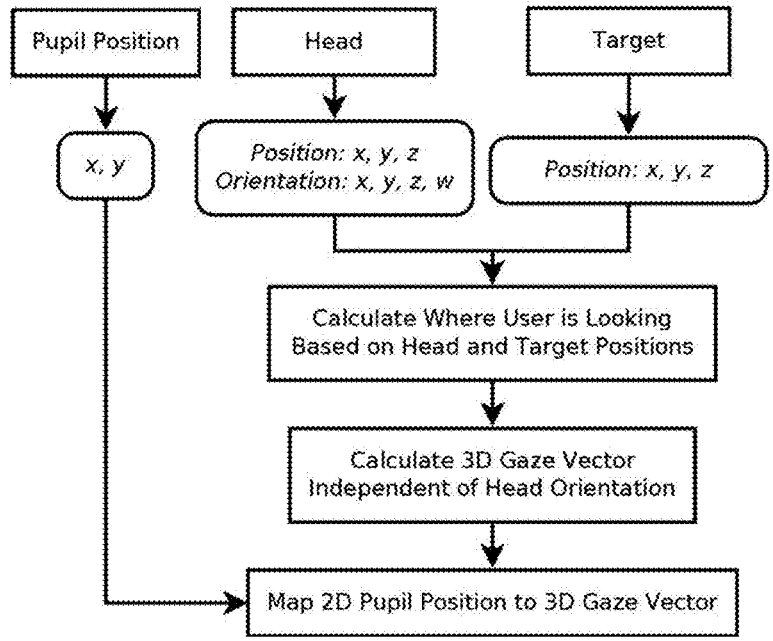
FIG. 18 is a flow chart of a calibration sub-step of a 3D gaze vector determination step performed by the computer of the system of FIG. 1, prior to runtime of a surgical procedure.
Figure 19:
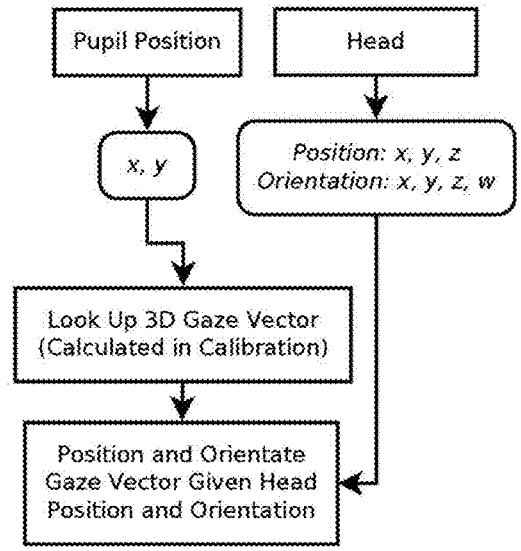
FIG. 19 is a flow-chart of an interpolation sub-step of a 3D gaze vector determination step performed by the computer of the system of FIG. 1, during runtime of a surgical procedure.

In an exemplary embodiment, the determination of the 3D gaze vector is implemented in two sub-steps, as shown in FIGS. 18 and 19.

In the first sub-step shown in FIG. 18, performed prior to runtime of the manual task, a sample of known 3D gaze vectors is generated during a calibration process wherein the surgeon fixates on the centroid of a tracking object in a variety of known positions, and the gaze vector is calculated between the surgeon's head and the tracking object. This vector is normalized so that the distance between the head and the tracking object is not a factor. The inverse transformation of the head position and orientation is then applied to the vector. This ensures that the position and orientation of the head does not affect the calibration. Finally, the known gaze vector is saved in the database, with the associated known 2D coordinates of the current field of view (FOV) position streamed from the pupil tracking subsystem (20). In exemplary embodiment, at least ten calibration positions spanning the surgeon's FOV may be obtained.

In the second sub-step shown in FIG. 19, performed during runtime of the manual task, interpolation may be used to determine a 3D gaze vector for a given combination of pupil position data in the FOV streamed from the pupil tracking subsystem (20), and position and directional data streamed from the head tracking subsystem (30).

Figure 20:
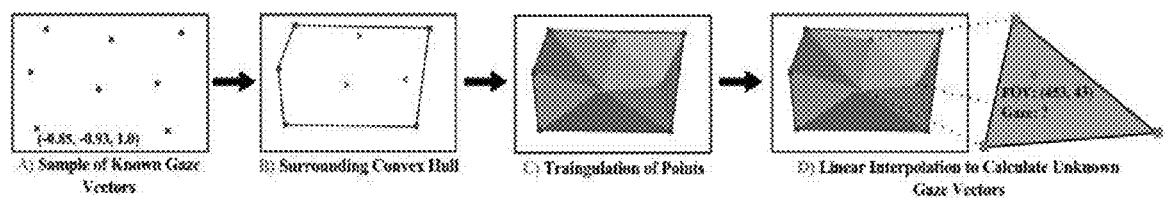
FIG. 20 is a schematic representation of the interpolation sub-step of FIG. 19.

FIG. 20 illustrates the interpolation process. Beginning with the sample of known FOV (x, y) coordinate points associated with a known associated gaze vector, as shown in FIG. 20, part (a), the computer (100) first solves for the convex hull surrounding the known FOV coordinate points as shown in FIG. 20, part (b). Next, the computer (100) triangulates the points of the known FOV coordinate points, while maintaining the outer convex hull as shown in FIG. 20, part (c). Finally, the computer (100) performs a linear interpolation between the three points of each triangle as shown in FIG. 20, part (d). During the interpolation step, the computer (100) calculates the eye gaze vector for a particular position in the FOV as determined by the pupil tracking subsystem (20). This allows the computer (100) to quickly "look up" the gaze vector when given the FOV coordinates from the pupil tracking subsystem (20).

Example 1: Accuracy of Determined 3D Gaze Vector

In this example, the accuracy of the 3D gaze vector determined by the system (10) is determined by comparing its position to arrays of known points.

As shown in FIG. 21, a three-dimensional physical marker array of nine 12 mm passive IR reflective markers was constructed. The passive IR reflective markers are elevated above a board with wooden dowels and arranged in a 3×3 array. The height of each marker was randomized and spanned a range of zero to 30 cm above the surface of the board. This back edge of this platform was positioned 70 cm from the human participant and the OptiTrack™ system of the head tracking subsystem (30) was used to accurately determine the position of each marker as a point in 3D space. An audio file was used to provide a standardized cue for each participant to fixate on the next marker in the physical array.

As well, a MATLAB™ script was developed to display a sequence of virtual markers in a virtual marker array comprising 15 circles on a 24" widescreen computer monitor. These virtual markers were evenly distributed in a 3×5 array. In order to determine the physical position of each virtual marker, the dot pitch of a computer monitor (0.38 mm) was used to translate the pixel address of each marker into a physical position measured from pixel (0,0) at the upper left corner of the monitor. The position of pixel (0,0) relative to one of three IR markers placed on the bezel of the computer monitor was also measured. (FIG. 22 shows the positioning of one of the IR markers with respect to the screen edge of the computer monitor.) Each virtual marker was displayed on the computer monitor individually for 3000 ms and plotted in a linear sequence from left to right along each row starting at the upper left of the computer monitor screen.

Subjects performed all testing from a seated position. The 2D calibration of the pupil tracking subsystem (20) was performed using the corners of the monitor at an initial viewing distance of 55 cm. Next, the IR markers on the computer monitor, pupil tracking subsystem (20) and a calibration triangle were selected and registered as rigid bodies in the Motive™ software of the head tracking subsystem (30). A set of known calibration vectors were then recorded by moving the calibration triangle throughout the participant's field of view. Participants were instructed to fixate their eye gaze on the centroid of the calibration triangle as it moved to each calibration position.

A MATLAB™ script was performed to obtain spatial coherence between the different coordinate systems. The origin of the eye gaze vector was translated to the approximate the back of the subject's retina from the centroid of the tracked triangle representing head position, using the average reported diameter of an adult eye ball.

The data was visualized using MATLAB™ 3 D graph functions in order to confirm that spatial coherence had been obtained. Euclidean distance was determined by solving for the minimal distance between the line represented by the eye gaze vector and a point in 3D space represented by a given a marker of the physical array or virtual array. The gaze angle error was determined by comparing the ideal gaze angle represented by the eye gaze vector originating from the eye to the marker position.

Figure 23:
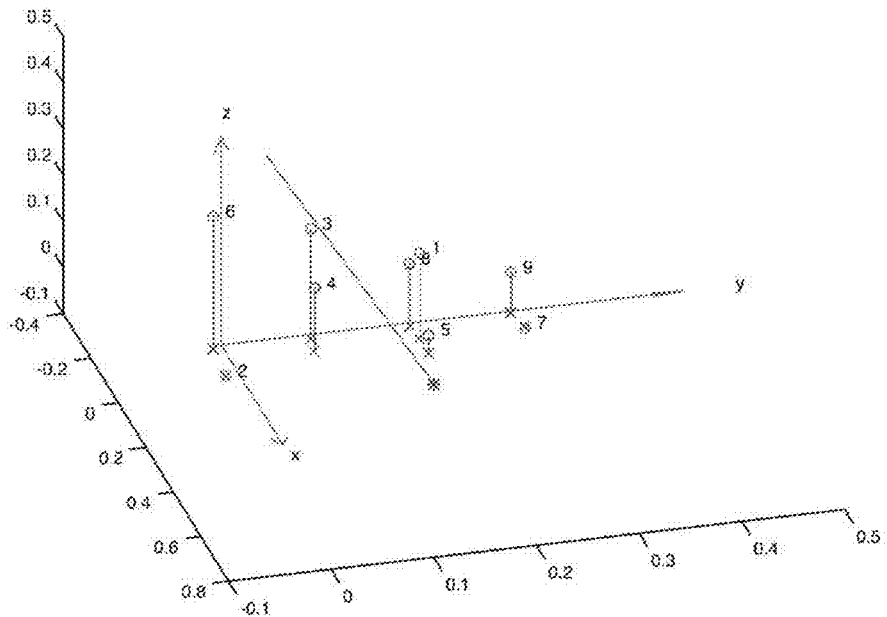
FIG. 23 shows a MATLAB™ visualization of the physical IR marker array of FIG. 21, and a 3D gaze vector for physical IR marker 3, as determined for a single participant in an experiment with the system of FIG. 2.
Figure 24:
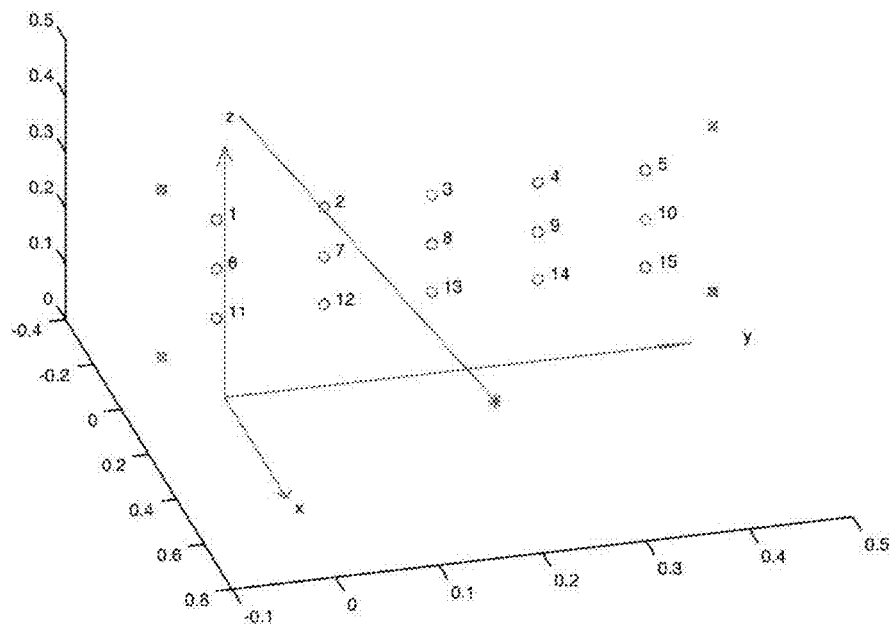
FIG. 24 shows a MATLAB™ visualization of the virtual marker positions displayed on the computer monitor of FIG.

FIG. 23 shows a MATLAB™ visualization of the physical IR marker array and eye gaze vector in line with physical marker number 3, with each axis representing distance in meters. FIG. 24 shows a MATLAB™ visualization of the virtual marker positions displayed on the LCD monitor and gaze vector in line with virtual marker number 2, with each axis representing distance in meters. In both FIGS. 23 and 24, the origin of the eye gaze vector is represented by *. The eye gaze vector is represented as a 1 m long line extending towards the gaze targets represented by ○. Distance and gaze angle error were determined for each participant at a single distance for the physical marker array and at three distances for virtual marker array.

FIG. 25 delineates the Euclidian distance and visual angle error for a single participant for the physical marker array. The pooled mean distances and angle error for each physical marker and virtual marker are summarized in FIGS. 26 and 27, respectively. The overall accuracy for 3D gaze vector from data pooled for all three viewing distances was 2.78±1.6 cm for the physical marker array and 2.49±0.95 cm for the virtual marker array.

Example 1 demonstrates the development of an accurate 3D gaze tracking system (10) by integrating 2D pupil tracking technology with three-dimensional positional and directional optical head tracking for viewing objects at a focal distance of 55-85 cm. The synchronization and recording software allows retention of all of the information streamed from the Dikablis™ recorder regarding 2D fixation, pupil size, and timestamp information. This information could be used to determine fixation duration and other traditional eye tracking metrics.

Inspection of the gaze accuracy data revealed decreased accuracy for both physical and virtual markers near the periphery of the subject's vision. Without restriction to a theory, this is believed to be attributable to the following reasons. The Dikablis™ Eye Tracker employed utilizes a linear calibration method for both (x,y) gaze coordinates. At more extreme gaze angles, where the eye is focused on objects to the extreme left or right for example, there are some torsional movements of the eye. Based on the calibration method it is likely that these movements resulted in a less accurate determination of gaze direction. While the method of generating multiple eye gaze vectors likely compensated for some of this error, it also performed a linear calibration based on a convex hull for both x and y coordinates. Future optimization of this method may involve measuring and correcting for torsional or non-linear gaze deviation at more extreme gaze angles.

A decrease in gaze accuracy for markers below the horizon of some subject's gaze was also measured. Without restriction to a theory, this was likely due to an inaccurate determination of the pupil's centre by the Dikablis Recorder™ software. Despite numerous attempts to optimize the position of the eye tracking camera on the Dikablis™, the inventors were sometimes forced to position the camera closer to the individual's gaze horizon. This resulted in a reflection of the IR emitter just below the eye camera (22) in the image of the subject's eye and pupil. Following the initial manual 2D calibration of the eye tracker, there was a discrepancy in the plotted gaze position for targets towards the lower portion of a subject's field of view when this reflection in the pupil was significant. Despite attempts to reduce the intensity of the IR LED intensity, this appeared to reduce the accuracy of the system for some subjects.

Visual inspection of the IR spectrum in the Dikablis Recorder™ software during pupil detection calibration demonstrated a significant amount of noise. There appeared to be an oscillation in the overall amplitude of the spectrum on the order of 1-2 Hz. The use of an AC power conditioner or DC power source appeared to reduce the intensity of this noise. For all of the accuracy testing in this example, a DC power source from a lithium polymer battery was used.

Example No. 2: Recording of Synchronized Eye Gaze and Hand Data

Experiments were carried out to demonstrate the recording of synchronized 3D gaze and hand data (kinematics and forces) during a simulated surgical task of placing three interrupted sutures in a marked location of 3-Dmed™ (3-Dmed, Franklin, Ohio) synthetic skin, in a simulated work surgical area as shown in FIG. 28.

The system (10) was calibrated and each participant was fitted with the pupil tracking subsystem (20), head tracking subsystem (30), and the hand tracking subsystem (40) as described above. Further, Adson forceps (64) with integrated force sensors of the instrument force tracking system (60) were provided for the suturing task. A Canon™ digital SLR camera, being both a video recorder and an audio recorder, was used to generate audio and video signals encoding for sounds and images of each participant performing the simulated task, which signals were recorded to the database. In order to assist with modeling of each subject's hands, the positions of each MCP, PIP and DIP joint in both hands were marked with a permanent marker and photographed adjacent to a ruler for scale.

Prior to completing the simulated surgical task, each participant was asked to direct their gaze to the center of the starting positions for each instrument and place their right index finger at the same position. This generated the data necessary for validating the accuracy of the synchronized pupil tracking subsystem (20), head tracking subsystem (30), and hand tracking subsystem (40).

Instruments including forceps (64) with integrated force sensors, a needle driver, and scissors (62) were provided. Each instrument was placed on the board in a marked and labeled home/target position. Participants were instructed to perform an instrument tie for making their surgical knots and to place each instrument back in the designated starting position when not in use. This resulted in a sequence of grasping the forceps (64) and driver initially, returning the forceps (64) second, and returning the driver before grasping the scissors (62) to complete the task. This forced each participant to decompose the major steps of the suturing task into discrete and easy to identify segments.

To determine the accuracy of the pupil tracking subsystem (20) when positioned over the surgical simulation area and of the hand tracking system (40), the center of each of the instrument's home positions was taken as a physical target. Video of the accuracy task was used to determine the approximate time corresponding to the mid-point of gaze fixation and finger positioning over a particular target. A 250 ms sample of gaze data was taken around each time point, filtered using MATLAB's median filter (medfilt1), and the average Euclidean distance and standard deviation was determined. A similar 250 ms sample of position data for the EM sensor (42) of the hand tracking subsystem (40) corresponding to the index finger of the right hand (RightD2) was used to determine the accuracy of the hand tracking subsystem (40). The EM sensor (42) data did not require filtering.

Calibration of the OptiTrack MoCap™ system of the head tracking system (30) typically resulted in a triangulation residual mean error of <0.2 mm as reported by Motive™ software. Calibration of the Dikablis™ eye tracker of the pupil tracking system (10) was completed with 25 gaze vectors using a calibration target composed of 3 IR markers arranged in an asymmetric triangle. The TrakSTAR™ EM sensor (42) of the hand tracking subsystem (40) was aligned with the OptiTrack™ frame of reference by inverting a designated finger and placing it over the three IR markers representing the ground plane. Following capture of the accuracy and suturing task, the synchronized data was saved to file in XML format. A MATLAB script was then used to parse the raw data and load the necessary elements for further analysis into MATLAB arrays.

Visualization of the raw data on a computer display device was accomplished by reconstructing both the 3D gaze vector and hand model from the pupil tracking subsystem (20), head tracking subsystem (30), and hand tracking subsystem (40) data respectively. While the finger tips were plotted as points in 3D space, the palm was drawn as a six sided polygon and rotated according to the quaternion rotation data encoded by the EM sensor (42) of the hand tracking system (40) for the sixth marker on each hand. This marker corresponds to the dorsal aspect of the midpoint of the third metacarpal.

FIG. 29 shows the MATLAB™ 3 D visualization of the hands and eye gaze vector with respect to the instrument home positions and accuracy targets. Here the corrected origin of the 3D gaze vector is represented by * and a 1 m line extending towards the fixation point. The intersection of this vector with the ground plane can be used to determine a fixation point if the physical location of the surface is known. For testing the accuracy of the eye gaze vector, the Euclidean distance between a line (the eye gaze vector) and a point (the marked center of each target) was calculated based on Equation 2 below, $$D = \frac{|(x_0 - x_1) - (x_0 - x_2)|}{|(x_2 - x_1)|} \qquad (2)$$

where $x_1=(x_1,y_1,z_1)$ and $x_2=(x_2,y_2,z_2)$ are two points on the vector and $x_0=(x_0,y_0,z_0)$ is a point in Euclidean space, $\mathbb{R}^3$.

Both video and the distance over time curve can be inspected to determine when the gaze is fixated on a particular target. FIG. 30 shows a series of graphs comparing the distance between the eye vector and each target over the course of the experiment for a single subject, wherein participants fixated on three instrument home positions/targets in sequence. The participants were prompted to move from one target to the next in sequence so the distance approaches zero in sequence, as expected. FIG. 31 is a graph of gaze deviation for all participants for three targets. FIG. 32 summarizes the 3D gaze accuracy for all three participants relative to the three targets.

Further, the EM sensor (42) data of the hand tracking subsystem (40) for the right second digit (index finger) was evaluated for accuracy. The three dimensional coordinates for this sensor were translated +1 cm in the MATLAB z-axis to correct for the placement of the EM sensor (42) over the fingernail and not the finger pad. The Euclidean distance, D, between two points was then determined as per equation (3), below $$D=\sqrt{(x_2-x_1)^2+(y_2-y_1)^2+(z_2-z_1)^2} \quad (3)$$

where $x_n, y_n, z_n$ are the coordinates of a point in Euclidean space, $\mathbb{R}^3$ (120).

FIG. 33 shows the distance between the right index finger and the three accuracy targets for a single participant. FIG. 34 shows the finger position accuracy for all three participants. FIG. 35 summarizes the finger position accuracy data for all three participants. Overall, the pooled 3D gaze vector and EM sensor (42) finger tip deviations were 4.0±1 cm and 0.91±0.09 cm, respectively.

This example demonstrates the successful acquisition of synchronized eye gaze and hand motion data while performing a complex bimanual task. This system (10) was designed for acquiring eye gaze and hand data from individuals performing surgical tasks, but may also be used to acquire eye gaze and hand data for other complex bimanual tasks. The numerous sensors on each hand allow for recording of highly detailed motion information necessary for characterizing specific hand gestures. The system (10) may be used to discriminate between persons with different levels of experience using similar descriptive statistics, and provide additional information regarding specific portions of a maneuver. The system (10) provides a rich data set to analyze the kinematics of a manual task including the orientation of each hand and finger during a specific subtask. In addition, the 3D gaze acquisition system (10) can acquire precision visual information regarding gaze behaviour. Spatially related and temporally coherent eye gaze and hand data (kinematics and applied force) permits evaluation of eye hand interaction and coordination.

Alternative Embodiments

In alternative embodiments, the hand tracking subsystem (30) may comprise sensors that operate on optical sensing principles. For example, such sensors may comprise a Leap Motion Controller™ (Leap Motion, Inc., San Francisco, Calif.) or a Microsoft Kinect Sensor™ (Microsoft Corp., Redmond, Wash.). Unlike the Trakstar™ electromagnetic sensor, these optical tracking methods require a direct line of sight, and may therefore produce less accurate results. With this caveat in mind, raw tracking data from a Leap or Kinect can be calibrated and aligned with the rest of the system.

To calibrate the Microsoft Kinect Sensor™ or similar technology with the optical head tracking subsystem (30). One can point the Microsoft Kinect Sensor™ at an L-Frame with three optical IR markers registered to the OptiTrack™ system described above. An IR marker should be placed at each corner of the L-Frame. In the image given from the Microsoft Kinect Sensor™, the user can select the three markers of the L-Frame. Due to the Microsoft Kinect Sensor's™ depth capturing capabilities the positions of these IR markers relative to the Microsoft Kinect Sensor™ can be captured. The reason for choosing an L-shape is that by knowing the distances between the points, one can solve what points correspond to each other in the two systems. By knowing what points correspond to one another allows the system solve the transformation from the Microsoft Kinect Sensor™ space to the system space. If another shape is chosen then an algorithm like an iterative closest point algorithm could be used to solve the transformation.

The Leap Motion Controller™ can be calibrated by pointing the Leap Motion Controller™ at an L-Frame with three optical IR markers registered to the OptiTrack™ system described above. Next, the subject may move their index finger to each of the IR markers. Finally the same approach described in the Kinect™ calibration can be used to transform the Leap Motion Controller™ data from the Leap Motion Controller™ space to the system space.

After the Leap Motion Controller™ or Microsoft Kinect Sensor™ system is calibrated, both can provide the positions of the fingers and hands of the subject. The Microsoft Kinect Sensor™ can also send a point cloud showing a full 3D scan of the environment. If the Microsoft Kinect Sensor™ is directed at the subject's head it could be used to track head position as a substitute for the OptiTrack™ IR tracking system of the head tracking subsystem described above. However, the accuracy of eye gaze tracking may be significantly reduced using this approach.

It will be appreciated that the present invention may be implemented as a computer program product that comprises a computer program mechanism embedded in a computer readable storage medium. For instance, the computer program product could contain program modules. These program modules may be stored on CD-ROM, DVD, magnetic disk storage product, flash media or any other computer readable data or program storage product. The software modules in the computer program product may also be distributed electronically, via the Internet or otherwise, by transmission of a data signal (in which the software modules are embedded) such as embodied in a carrier wave.

The present invention has been described above and shown in the drawings by way of exemplary embodiments and uses, having regard to the accompanying drawings. The exemplary embodiments and uses are intended to be illustrative of the present invention. It is not necessary for a particular feature of a particular embodiment to be used exclusively with that particular exemplary embodiment. Instead, any of the features described above and/or depicted in the drawings can be combined with any of the exemplary embodiments, in addition to or in substitution for any of the other features of those exemplary embodiments. One exemplary embodiment's features are not mutually exclusive to another exemplary embodiment's features. Instead, the scope of this disclosure encompasses any combination of any of the features. Further, it is not necessary for all features of an exemplary embodiment to be used. Instead, any of the features described above can be used, without any other particular feature or features also being used. Accordingly, various changes and modifications can be made to the exemplary embodiments and uses without departing from the scope of the invention as defined in the claims that follow.

The invention claimed is:

1. An eye gaze data capturing system for use with a human comprising a pupil, a head, and a hand, the system comprising:
 (a) a pupil tracking subsystem for tracking a pupil position in two-dimensions;
 (b) a head tracking subsystem for tracking a head position and orientation in three-dimensions;
 (c) an instrument force tracking subsystem for tracking a hand force applied to a hand-held instrument;
 (d) a suture force tracking subsystem for tracking a tension force applied by the hand to a suture thread; and
 (e) a computer comprising a processor operatively connected to the pupil tracking subsystem, the head tracking subsystem, the instrument force tracking subsystem, and the suture force tracking subsystem, and a memory comprising a non-transitory medium storing instructions readable by the processor to implement a method comprising the continuously performed steps of:
(i) determining an eye gaze vector based on the pupil position, and the head position and orientation; and
(ii) recording to a database in the memory a record of spatially and temporally coherent data comprising the eye gaze vector, the hand force, and the tension force.

2. The system of claim 1 wherein the instrument force tracking subsystem comprises a piezoelectric sensor attachable to the hand-held instrument.

3. An eye gaze and hand data capturing system for use with a human comprising a pupil, a head, and a hand, the system comprising:
(a) a pupil tracking subsystem for tracking a pupil position in two-dimensions;
(b) a head tracking subsystem for tracking a head position and orientation in three-dimensions;
(c) a hand tracking subsystem for tracking a hand position and orientation in three-dimensions;
(d) a suture force tracking subsystem for tracking a tension force applied by the hand to a suture thread; and
(e) a computer comprising a processor operatively connected to the pupil tracking subsystem, the head tracking subsystem, and the suture force tracking subsystem, and a memory comprising a non-transitory medium storing instructions readable by the processor to implement a method comprising the repeatedly performed steps of:
(i) determining an eye gaze vector based on the pupil position, and the head position and orientation; and
(ii) recording to a database in the memory a record of spatially and temporally coherent data comprising the eye gaze vector, the hand position, and the tension force.

4. The system of claim 3 wherein the pupil tracking subsystem comprises an eye camera for optically monitoring the pupil position.

5. The system of claim 3 wherein the head tracking subsystem comprises a plurality of markers attachable to the head, and at least one camera for optically capturing a position of the plurality of markers.

6. The system of claim 3 wherein the hand tracking subsystem comprises at least one electromagnetic sensor attachable to the hand, and at least one electromagnetic transmitter for generating an electromagnetic field detectable by the electromagnetic sensor.

7. The system of claim 6 wherein the at least one electromagnetic sensor comprises a plurality of electromagnetic sensors, wherein each of the sensors is attached to a different part of the hand for tracking positions and orientations of different parts of the hand.

8. The system of claim 7 where the different parts of the hand comprise different fingers of the hand.

9. The system of claim 8 wherein the different parts of the hand further comprise a dorsum of the hand.

10. The system of claim 3 wherein determining the eye gaze vector comprises:
(a) storing in the memory a plurality of known pairs of associated pupil positions and eye gaze vectors; and
(b) interpolating the eye gaze vector based on the stored plurality of known pairs of associated pupil positions and eye gaze vectors.

11. The system of claim 3 wherein:
(a) the system further comprises at least one video recorder for generating a video signal encoding an image of the hand, wherein the processor is further operatively connected to the video recorder; and
(b) recording to the database further comprises recording the video signal to the record as part of the temporally coherent data.

12. The system of claim 11 wherein the at least one camera is positioned to capture the image from a viewpoint approximating the point of view of the pupil.

13. The system of claim 11 wherein the at least one camera is positioned to capture the image from a viewpoint other than the viewpoint approximating the point of view of the pupil.

14. The system of claim 3 wherein:
(a) the system further comprises at least one audio recorder for generating an audio signal encoding a sound of the human, wherein the processor is further operatively connected to the audio recorder; and
(b) recording to the database further comprises recording the audio signal to the record as part of the temporally coherent data.

* * * * *